US012562268B2

(12) United States Patent
    Fryman et al.

(10) Patent No.: US 12,562,268 B2
(45) Date of Patent: Feb. 24, 2026

(54) LOCATION-BASED RECONFIGURATION OF INFUSION PUMP SETTINGS

(71) Applicant: ICU Medical, Inc., San Clemente, CA (US)

(72) Inventors: Marshall E. Fryman, Libertyville, IL (US); Matteo D. Picinich, Temecula, CA (US); Anandaraman Vithyananthan, Chennai (IN); Syedjavid Syed Khadar, Tirupur (IN); Ujjawal Kumar, Gurugram (IN)

(73) Assignee: ICU Medical, Inc., San Clemente, CA (US)

( * ) Notice: Subject to any disclaimer, the term of this patent is extended or adjusted under 35 U.S.C. 154(b) by 1012 days.

(21) Appl. No.: 17/305,035

(22) Filed: Jun. 29, 2021

(65) Prior Publication Data

US 2022/0037011 A1     Feb. 3, 2022

Related U.S. Application Data

(60) Provisional application No. 63/068,798, filed on Aug. 21, 2020.

(30) Foreign Application Priority Data

Jul. 2, 2020    (IN) .............................. 202011028208

(51) Int. Cl.
    *G16H 40/63* (2018.01)
    *G16H 20/17* (2018.01)
    *G16H 40/67* (2018.01)
(52) U.S. Cl.
    CPC ............. *G16H 40/63* (2018.01); *G16H 20/17* (2018.01); *G16H 40/67* (2018.01)

(58) Field of Classification Search
    CPC ......... G16H 40/63; G16H 20/17; G16H 40/67
    See application file for complete search history.

(56) References Cited

U.S. PATENT DOCUMENTS 4,024,864 A     5/1977   Davies et al.
4,055,175 A    10/1977   Clemens et al.
                 (Continued)

FOREIGN PATENT DOCUMENTS

AU     2004226440      10/2004
AU     2004305087      7/2005
                 (Continued)

OTHER PUBLICATIONS

Ahn et al., To"wards Scalable Authentication in Health Services", Eleventh IEEE International Workshops on Enabling Technologies: Infrastructure for Collaborative Enterprises, Jun. 2002, pp. 83-88.
                 (Continued)

*Primary Examiner* — Bhisma Mehta
*Assistant Examiner* — Haden Matthew Ritchie
(74) *Attorney, Agent, or Firm* — Knobbe, Martens, Olson & Bear, LLP

(57)                    ABSTRACT

A system configured to reconfigure the settings on a medical device based on a detected location of the medical device is provided. The system may include a server configured to receive a connection request from a medical device, update the settings on the medical device, determine that the medical device has entered another geographical area, and transmit, to the medical device, additional settings that can be used to connect to another server configured to communicate with medical devices in said another geographical area.

20 Claims, 7 Drawing Sheets

(56)                    References Cited

U.S. PATENT DOCUMENTS

| | | | |
|---|---|---|---|
| 4,151,845 A | 5/1979 | Clemens |
| 4,213,454 A | 7/1980 | Shim |
| 4,240,438 A | 12/1980 | Updike et al. |
| 4,280,494 A | 7/1981 | Cosgrove et al. |
| 4,308,866 A | 1/1982 | Jeliffe |
| 4,370,983 A | 2/1983 | Lichtenstein et al. |
| 4,373,527 A | 2/1983 | Fischell |
| 4,392,849 A | 7/1983 | Petre et al. |
| 4,395,259 A | 7/1983 | Prestele et al. |
| 4,457,751 A | 7/1984 | Rodler |
| 4,464,170 A | 8/1984 | Clemens |
| 4,469,481 A | 9/1984 | Kobayashi |
| 4,475,901 A | 10/1984 | Kraegen et al. |
| 4,494,950 A | 1/1985 | Fischell |
| 4,498,843 A | 2/1985 | Schneider et al. |
| 4,515,584 A | 5/1985 | Abe et al. |
| 4,526,568 A | 7/1985 | Clemens et al. |
| 4,529,401 A | 7/1985 | Leslie et al. |
| 4,543,955 A | 10/1985 | Schroeppel |
| 4,551,133 A | 11/1985 | Zegers de Beyl et al. |
| 4,553,958 A | 11/1985 | LeCocq |
| 4,559,037 A | 12/1985 | Franetzki et al. |
| 4,613,937 A | 9/1986 | Batty |
| 4,624,661 A | 11/1986 | Arimond |
| 4,633,878 A | 1/1987 | Bombardieri |
| 4,634,426 A | 1/1987 | Kamen |
| 4,634,427 A | 1/1987 | Hannula et al. |
| 4,674,652 A | 6/1987 | Aten et al. |
| 4,676,776 A | 6/1987 | Howson et al. |
| 4,679,562 A | 7/1987 | Luksha |
| 4,685,903 A | 8/1987 | Cable et al. |
| 4,695,954 A | 9/1987 | Rose |
| 4,696,671 A | 9/1987 | Epstein et al. |
| 4,714,462 A | 12/1987 | DiDomenico |
| 4,722,734 A | 2/1988 | Kolin |
| 4,730,849 A | 3/1988 | Siegel |
| 4,731,051 A | 3/1988 | Fischell |
| 4,741,732 A | 5/1988 | Crankshaw et al. |
| 4,756,706 A | 7/1988 | Kerns et al. |
| 4,776,842 A | 10/1988 | Franetzki et al. |
| 4,785,969 A | 11/1988 | McLaughlin |
| 4,803,625 A | 2/1989 | Fu et al. |
| 4,835,372 A | 5/1989 | Gombrich et al. |
| 4,838,275 A | 6/1989 | Lee |
| 4,838,856 A | 6/1989 | Mulreany et al. |
| 4,838,857 A | 6/1989 | Strowe et al. |
| 4,854,324 A | 8/1989 | Hirschman et al. |
| 4,857,716 A | 8/1989 | Gombrich et al. |
| 4,858,154 A | 8/1989 | Anderson et al. |
| 4,898,578 A | 2/1990 | Rubalcaba, Jr. |
| 4,908,017 A | 3/1990 | Howson et al. |
| 4,933,873 A | 6/1990 | Kaufman et al. |
| 4,943,279 A | 7/1990 | Samiotes et al. |
| 4,946,439 A | 8/1990 | Eggers |
| 4,953,745 A | 9/1990 | Rowlett |
| 4,978,335 A | 12/1990 | Arthur, III |
| 5,000,739 A | 3/1991 | Kulisz et al. |
| 5,010,473 A | 4/1991 | Jacobs |
| 5,014,698 A | 5/1991 | Cohen |
| 5,016,172 A | 5/1991 | Dessertine |
| 5,026,084 A | 6/1991 | Paisfield |
| 5,034,004 A | 7/1991 | Crankshaw |
| 5,041,086 A | 8/1991 | Koenig et al. |
| 5,058,161 A | 10/1991 | Weiss |
| 5,078,683 A | 1/1992 | Sancoff et al. |
| 5,084,828 A | 1/1992 | Kaufman et al. |
| 5,088,981 A | 2/1992 | Howson et al. |
| 5,097,505 A | 3/1992 | Weiss |
| 5,100,380 A | 3/1992 | Epstein et al. |
| 5,102,392 A | 4/1992 | Sakai et al. |
| 5,104,374 A | 4/1992 | Bishko et al. |
| 5,109,850 A | 5/1992 | Blanco et al. |
| 5,131,816 A | 7/1992 | Brown |
| 5,142,484 A | 8/1992 | Kaufman et al. |
| 5,153,827 A | 10/1992 | Coutre et al. |
| 5,157,640 A | 10/1992 | Backner |
| 5,161,222 A | 11/1992 | Montejo et al. |
| 5,177,993 A | 1/1993 | Beckman et al. |
| 5,181,910 A | 1/1993 | Scanlon |
| 5,190,522 A | 3/1993 | Wocicki et al. |
| 5,199,439 A | 4/1993 | Zimmerman et al. |
| 5,200,891 A | 4/1993 | Kehr et al. |
| 5,216,597 A | 6/1993 | Beckers |
| 5,221,268 A | 6/1993 | Barton et al. |
| 5,230,061 A | 7/1993 | Welch |
| 5,243,982 A | 9/1993 | Möstl et al. |
| 5,244,463 A | 9/1993 | Cordner, Jr. et al. |
| 5,249,260 A | 9/1993 | Nigawara et al. |
| 5,254,096 A | 10/1993 | Rondelet et al. |
| 5,256,156 A | 10/1993 | Kern et al. |
| 5,256,157 A | 10/1993 | Samiotes et al. |
| 5,261,702 A | 11/1993 | Mayfield |
| 5,317,506 A | 5/1994 | Coutre et al. |
| 5,319,355 A | 6/1994 | Russek |
| 5,319,363 A | 6/1994 | Welch et al. |
| 5,330,634 A | 7/1994 | Wong et al. |
| 5,338,157 A | 8/1994 | Blomquist |
| 5,341,476 A | 8/1994 | Lowell |
| 5,364,346 A | 11/1994 | Schrezenmeir |
| 5,366,346 A | 11/1994 | Danby |
| 5,368,562 A | 11/1994 | Blomquist et al. |
| 5,373,454 A | 12/1994 | Kanda et al. |
| 5,376,070 A | 12/1994 | Purvis et al. |
| 5,378,231 A | 1/1995 | Johnson et al. |
| 5,389,071 A | 2/1995 | Kawahara et al. |
| 5,389,078 A | 2/1995 | Zalesky et al. |
| 5,417,222 A | 5/1995 | Dempsey et al. |
| 5,423,748 A | 6/1995 | Uhala |
| 5,429,602 A | 7/1995 | Hauser |
| 5,431,627 A | 7/1995 | Pastrone et al. |
| 5,432,777 A | 7/1995 | Le Boudec et al. |
| 5,445,621 A | 8/1995 | Poli et al. |
| 5,447,164 A | 9/1995 | Shaya et al. |
| 5,455,851 A | 10/1995 | Chaco et al. |
| 5,461,365 A | 10/1995 | Schlager et al. |
| 5,464,392 A | 11/1995 | Epstein et al. |
| 5,465,082 A | 11/1995 | Chaco |
| 5,485,408 A | 1/1996 | Blomquist |
| 5,486,286 A | 1/1996 | Peterson et al. |
| 5,493,430 A | 2/1996 | Lu et al. |
| 5,496,273 A | 3/1996 | Pastrone et al. |
| 5,505,828 A | 4/1996 | Wong et al. |
| 5,507,288 A | 4/1996 | Bocker et al. |
| 5,507,786 A | 4/1996 | Morgan et al. |
| 5,508,499 A | 4/1996 | Ferrario |
| 5,515,713 A | 5/1996 | Saugues et al. |
| 5,520,637 A | 5/1996 | Pager et al. |
| 5,522,798 A | 6/1996 | Johnson et al. |
| 5,547,470 A | 8/1996 | Johnson et al. |
| 5,554,013 A | 9/1996 | Owens et al. |
| 5,562,615 A | 10/1996 | Nassif |
| 5,577,169 A | 11/1996 | Prezioso |
| 5,582,323 A | 12/1996 | Kurtenbach |
| 5,582,593 A | 12/1996 | Hultman |
| 5,594,786 A | 1/1997 | Chaco et al. |
| 5,598,519 A | 1/1997 | Narayanan |
| 5,620,608 A | 4/1997 | Rosa et al. |
| 5,630,710 A | 5/1997 | Tune et al. |
| 5,636,044 A | 6/1997 | Yuan et al. |
| 5,643,212 A | 7/1997 | Coutre et al. |
| 5,651,775 A | 7/1997 | Walker et al. |
| 5,658,131 A | 8/1997 | Aoki et al. |
| 5,658,250 A | 8/1997 | Blomquist et al. |
| 5,665,065 A | 9/1997 | Colman et al. |
| 5,669,877 A | 9/1997 | Blomquist |
| 5,672,154 A | 9/1997 | Sillén et al. |
| 5,681,285 A | 10/1997 | Ford et al. |
| 5,685,844 A | 11/1997 | Marttila |
| 5,687,717 A | 11/1997 | Halpern et al. |
| 5,689,229 A | 11/1997 | Chaco et al. |
| 5,697,899 A | 12/1997 | Hillman et al. |
| 5,699,509 A | 12/1997 | Gary et al. |
| 5,708,714 A | 1/1998 | Lopez et al. |
| 5,713,350 A | 2/1998 | Yokota et al. |

(56)  References Cited

U.S. PATENT DOCUMENTS

| | | | |
|---|---|---|---|
| 5,713,856 A | 2/1998 | Eggers et al. |
| 5,718,562 A | 2/1998 | Lawless et al. |
| 5,719,761 A | 2/1998 | Gatti et al. |
| 5,733,259 A | 3/1998 | Valcke et al. |
| 5,738,102 A | 4/1998 | Lemelson |
| 5,744,027 A | 4/1998 | Connell et al. |
| 5,752,621 A | 5/1998 | Passamante |
| 5,754,111 A | 5/1998 | Garcia |
| 5,764,034 A | 6/1998 | Bowman et al. |
| 5,764,159 A | 6/1998 | Neftel et al. |
| 5,772,635 A | 6/1998 | Dastur et al. |
| 5,774,865 A | 6/1998 | Glynn |
| 5,778,256 A | 7/1998 | Darbee |
| 5,778,345 A | 7/1998 | McCartney |
| 5,781,442 A | 7/1998 | Engleson et al. |
| 5,782,805 A | 7/1998 | Meinzer et al. |
| 5,788,669 A | 8/1998 | Peterson |
| 5,797,515 A | 8/1998 | Liff et al. |
| 5,800,387 A | 9/1998 | Duffy et al. |
| 5,814,015 A | 9/1998 | Gargano et al. |
| 5,822,544 A | 10/1998 | Chaco et al. |
| 5,822,715 A | 10/1998 | Worthington et al. |
| 5,827,179 A | 10/1998 | Lichter et al. |
| 5,832,448 A | 11/1998 | Brown |
| 5,836,910 A | 11/1998 | Duffy et al. |
| 5,850,344 A | 12/1998 | Conkright |
| 5,867,821 A | 2/1999 | Ballantyne et al. |
| 5,870,733 A | 2/1999 | Bass et al. |
| 5,871,465 A | 2/1999 | Vasko |
| 5,873,731 A | 2/1999 | Predergast |
| 5,885,245 A | 3/1999 | Lynch et al. |
| 5,897,493 A | 4/1999 | Brown |
| 5,897,498 A | 4/1999 | Canfield, II et al. |
| 5,910,252 A | 6/1999 | Truitt et al. |
| 5,912,818 A | 6/1999 | McGrady et al. |
| 5,915,240 A | 6/1999 | Karpf |
| 5,920,054 A | 7/1999 | Uber, III |
| 5,920,263 A | 7/1999 | Huttenhoff et al. |
| 5,924,074 A | 7/1999 | Evans |
| 5,931,764 A | 8/1999 | Freeman et al. |
| 5,935,099 A | 8/1999 | Peterson et al. |
| 5,935,106 A | 8/1999 | Olsen |
| 5,941,846 A | 8/1999 | Duffy et al. |
| 5,956,501 A | 9/1999 | Brown |
| 5,957,885 A | 9/1999 | Bollish et al. |
| 5,960,085 A | 9/1999 | de la Huerga |
| 5,961,448 A | 10/1999 | Swenson et al. |
| 5,967,559 A | 10/1999 | Abramowitz |
| 5,971,594 A | 10/1999 | Sahai et al. |
| 5,975,081 A | 11/1999 | Hood et al. |
| 5,990,838 A | 11/1999 | Burns et al. |
| 5,997,476 A | 12/1999 | Brown |
| 6,000,828 A | 12/1999 | Leet |
| 6,003,006 A | 12/1999 | Colella et al. |
| 6,012,034 A | 1/2000 | Hamparian et al. |
| 6,017,318 A | 1/2000 | Gauthier et al. |
| 6,021,392 A | 2/2000 | Lester et al. |
| 6,024,539 A | 2/2000 | Blomquist |
| 6,024,699 A | 2/2000 | Surwit et al. |
| 6,032,155 A | 2/2000 | de la Huerga |
| 6,032,676 A | 3/2000 | Moore |
| 6,039,251 A | 3/2000 | Holowko et al. |
| 6,070,761 A | 6/2000 | Bloom et al. |
| 6,073,106 A | 6/2000 | Rozen et al. |
| 6,104,295 A | 8/2000 | Gaisser et al. |
| 6,112,182 A | 8/2000 | Akers et al. |
| 6,112,323 A | 8/2000 | Meizlik et al. |
| RE36,871 E | 9/2000 | Epstein et al. |
| 6,115,365 A | 9/2000 | Newberg |
| 6,115,390 A | 9/2000 | Chuah |
| 6,122,536 A | 9/2000 | Sun et al. |
| 6,126,637 A | 10/2000 | Kriesel et al. |
| 6,135,949 A | 10/2000 | Russo et al. |
| 6,150,942 A | 11/2000 | O'Brien |
| 6,151,643 A | 11/2000 | Cheng et al. |
| 6,157,914 A | 12/2000 | Seto et al. |
| 6,159,147 A | 12/2000 | Lichter et al. |
| 6,167,567 A | 12/2000 | Chiles et al. |
| 6,182,667 B1 | 2/2001 | Hanks et al. |
| 6,189,105 B1 | 2/2001 | Lopes |
| 6,195,589 B1 | 2/2001 | Ketcham |
| 6,208,974 B1 | 3/2001 | Campbell et al. |
| 6,222,323 B1 | 4/2001 | Yamashita et al. |
| 6,223,440 B1 | 5/2001 | Rashman |
| 6,226,277 B1 | 5/2001 | Chuah |
| 6,227,371 B1 | 5/2001 | Song |
| 6,234,176 B1 | 5/2001 | Domae et al. |
| 6,241,704 B1 | 6/2001 | Peterson et al. |
| 6,248,067 B1 | 6/2001 | Causey, III et al. |
| 6,249,705 B1 | 6/2001 | Snell |
| 6,257,265 B1 | 7/2001 | Brunner et al. |
| 6,259,355 B1 | 7/2001 | Chaco et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,280,380 B1 | 8/2001 | Bardy |
| 6,283,761 B1 | 9/2001 | Joao |
| 6,285,665 B1 | 9/2001 | Chuah |
| 6,292,860 B1 | 9/2001 | Cochcroft, Jr. |
| 6,312,378 B1 | 11/2001 | Bardy |
| 6,327,254 B1 | 12/2001 | Chuah |
| 6,330,008 B1 | 12/2001 | Razdow et al. |
| 6,339,718 B1 | 1/2002 | Zatezalo et al. |
| 6,346,886 B1 | 2/2002 | de la Huerga |
| 6,363,282 B1 | 3/2002 | Nichols et al. |
| 6,371,719 B1 | 4/2002 | Hildebrandt |
| 6,377,548 B1 | 4/2002 | Chuah |
| 6,388,951 B1 | 5/2002 | Matsumoto et al. |
| 6,406,426 B1 | 6/2002 | Reuss et al. |
| 6,408,330 B1 | 6/2002 | de la Huerga |
| 6,418,334 B1 | 7/2002 | Unger et al. |
| 6,427,088 B1 | 7/2002 | Bowman et al. |
| 6,428,483 B1 | 8/2002 | Carlebach |
| 6,442,432 B2 | 8/2002 | Lee |
| 6,469,991 B1 | 10/2002 | Chuah |
| 6,475,180 B2 | 11/2002 | Peterson et al. |
| 6,482,158 B2 | 11/2002 | Mault |
| 6,485,418 B2 | 11/2002 | Yasushi et al. |
| 6,494,694 B2 | 12/2002 | Lawless et al. |
| 6,494,831 B1 | 12/2002 | Koritzinsky |
| 6,497,680 B1 | 12/2002 | Holst et al. |
| 6,514,460 B1 | 2/2003 | Fendrock |
| 6,517,482 B1 | 2/2003 | Elden et al. |
| 6,519,569 B1 | 2/2003 | White et al. |
| 6,520,930 B2 | 2/2003 | Critchlow et al. |
| 6,540,672 B1 | 4/2003 | Simonsen et al. |
| 6,542,902 B2 | 4/2003 | Dulong et al. |
| 6,544,212 B2 | 4/2003 | Galley et al. |
| 6,544,228 B1 | 4/2003 | Heitmeier |
| 6,546,350 B1 | 4/2003 | Hartmann et al. |
| 6,551,276 B1 | 4/2003 | Mann et al. |
| 6,554,798 B1 | 4/2003 | Mann et al. |
| 6,558,320 B1 | 5/2003 | Causey et al. |
| 6,558,351 B1 | 5/2003 | Steil et al. |
| 6,565,509 B1 | 5/2003 | Say et al. |
| 6,567,416 B1 | 5/2003 | Chuah |
| 6,571,294 B2 | 5/2003 | Simmon et al. |
| 6,572,542 B1 | 6/2003 | Houben et al. |
| 6,572,545 B2 | 6/2003 | Knobbe et al. |
| 6,578,002 B1 | 6/2003 | Derzay et al. |
| 6,581,117 B1 | 6/2003 | Klein et al. |
| 6,587,034 B1 | 7/2003 | Heiman et al. |
| 6,589,229 B1 | 7/2003 | Connelly et al. |
| 6,599,281 B1 | 7/2003 | Struys et al. |
| 6,602,191 B2 | 8/2003 | Quy |
| 6,605,072 B2 | 8/2003 | Struys et al. |
| 6,628,809 B1 | 9/2003 | Rowe et al. |
| 6,631,353 B1 | 10/2003 | Davis et al. |
| 6,640,246 B1 | 10/2003 | Gardy, Jr. et al. |
| 6,641,533 B2 | 11/2003 | Causey, III et al. |
| 6,647,299 B2 | 11/2003 | Bourget |
| 6,652,455 B1 | 11/2003 | Kocher |
| 6,653,937 B2 | 11/2003 | Nelson et al. |

(56)　　　References Cited

U.S. PATENT DOCUMENTS

| | | | |
|---|---|---|---|
| 6,659,947 | B1 | 12/2003 | Carter et al. |
| 6,669,630 | B1 | 12/2003 | Joliat et al. |
| 6,671,563 | B1 | 12/2003 | Engleson et al. |
| 6,673,033 | B1 | 1/2004 | Sciulli et al. |
| 6,674,403 | B2 | 1/2004 | Gray et al. |
| 6,681,003 | B2 | 1/2004 | Linder et al. |
| 6,689,091 | B2 | 2/2004 | Bui et al. |
| 6,692,241 | B2 | 2/2004 | Watanabe et al. |
| 6,694,191 | B2 | 2/2004 | Starkweather et al. |
| 6,694,334 | B2 | 2/2004 | DuLong et al. |
| 6,721,286 | B1 | 4/2004 | Williams et al. |
| 6,721,582 | B2 | 4/2004 | Trepagnier et al. |
| 6,725,200 | B1 | 4/2004 | Rost |
| 6,731,989 | B2 | 5/2004 | Engleson et al. |
| 6,740,072 | B2 | 5/2004 | Starkweather et al. |
| 6,751,651 | B2 | 6/2004 | Crockett |
| 6,752,787 | B1 | 6/2004 | Causey, III et al. |
| 6,753,830 | B2 | 6/2004 | Gelbman |
| 6,758,810 | B2 | 7/2004 | Lebel et al. |
| 6,773,396 | B2 | 8/2004 | Flach et al. |
| 6,774,786 | B1 | 8/2004 | Havekost et al. |
| 6,775,577 | B2 | 8/2004 | Cmkovich et al. |
| 6,780,156 | B2 | 8/2004 | Haueter et al. |
| 6,790,198 | B1 | 9/2004 | White et al. |
| 6,792,470 | B2 | 9/2004 | Hakenberg et al. |
| 6,796,956 | B2 | 9/2004 | Hartlaub et al. |
| 6,799,149 | B2 | 9/2004 | Hartlaub |
| 6,809,653 | B1 | 10/2004 | Mann et al. |
| 6,811,534 | B2 | 11/2004 | Bowman, IV et al. |
| 6,816,605 | B2 | 11/2004 | Rowe et al. |
| 6,839,753 | B2 | 1/2005 | Biondi et al. |
| 6,852,104 | B2 | 2/2005 | Blomquist |
| 6,859,134 | B1 | 2/2005 | Heiman et al. |
| 6,871,211 | B2 | 3/2005 | Labounty et al. |
| 6,873,268 | B2 | 3/2005 | Lebel et al. |
| 6,876,303 | B2 | 4/2005 | Reeder et al. |
| 6,885,881 | B2 | 4/2005 | Leonhardt |
| 6,891,525 | B2 | 5/2005 | Ogoro |
| 6,892,278 | B2 | 5/2005 | Ebergen |
| 6,899,695 | B2 | 5/2005 | Herrera |
| 6,915,170 | B2 | 7/2005 | Engleson et al. |
| 6,923,763 | B1 | 8/2005 | Kovatchev et al. |
| 6,924,781 | B1 | 8/2005 | Gelbman |
| 6,928,338 | B1 | 8/2005 | Buchser et al. |
| 6,928,490 | B1 | 8/2005 | Bucholz et al. |
| 6,936,029 | B2 | 8/2005 | Mann et al. |
| 6,945,954 | B2 | 9/2005 | Hochman et al. |
| 6,948,492 | B2 | 9/2005 | Wemeling et al. |
| 6,958,677 | B1 | 10/2005 | Carter |
| 6,958,691 | B1 | 10/2005 | Anderson et al. |
| 6,958,705 | B2 | 10/2005 | Lebel et al. |
| 6,961,448 | B2 | 11/2005 | Nichols et al. |
| 6,969,352 | B2 | 11/2005 | Chiang et al. |
| 6,969,865 | B2 | 11/2005 | Duchon et al. |
| 6,974,437 | B2 | 12/2005 | Lebel et al. |
| 6,979,326 | B2 | 12/2005 | Mann et al. |
| 6,980,958 | B1 | 12/2005 | Surwit et al. |
| 6,985,870 | B2 | 1/2006 | Martucci et al. |
| 6,986,347 | B2 | 1/2006 | Hickle |
| 6,997,880 | B2 | 2/2006 | Carlebach et al. |
| 6,997,920 | B2 | 2/2006 | Mann et al. |
| 6,998,984 | B1 | 2/2006 | Zittrain |
| 7,016,752 | B1 | 3/2006 | Ruben et al. |
| 7,017,293 | B2 | 3/2006 | Riley |
| 7,025,743 | B2 | 4/2006 | Mann et al. |
| 7,029,455 | B2 | 4/2006 | Flaherty |
| 7,038,584 | B2 | 5/2006 | Carter |
| 7,060,031 | B2 | 6/2006 | Webb et al. |
| 7,060,059 | B2 | 6/2006 | Keith et al. |
| 7,069,552 | B2 | 6/2006 | Lindberg et al. |
| 7,072,725 | B2 | 7/2006 | Bristol et al. |
| 7,079,035 | B2 | 7/2006 | Bock et al. |
| 7,092,943 | B2 | 8/2006 | Roese et al. |
| 7,096,072 | B2 | 8/2006 | Engleson et al. |
| 7,099,809 | B2 | 8/2006 | Dori |
| 7,103,419 | B2 | 9/2006 | Engleson et al. |
| 7,103,578 | B2 | 9/2006 | Beck et al. |
| 7,107,106 | B2 | 9/2006 | Engleson et al. |
| 7,108,680 | B2 | 9/2006 | Rohr et al. |
| 7,109,878 | B2 | 9/2006 | Mann et al. |
| 7,114,002 | B1 | 9/2006 | Okumura et al. |
| 7,117,041 | B2 | 10/2006 | Engleson et al. |
| 7,136,645 | B2 | 11/2006 | Hanson et al. |
| 7,137,964 | B2 | 11/2006 | Flaherty |
| 7,142,190 | B2 | 11/2006 | Martinez |
| 7,150,741 | B2 | 12/2006 | Erickson et al. |
| 7,153,289 | B2 | 12/2006 | Vasko |
| 7,154,397 | B2 | 12/2006 | Zerhusen et al. |
| 7,156,807 | B2 | 1/2007 | Carter et al. |
| 7,158,030 | B2 | 1/2007 | Chung |
| 7,161,484 | B2 | 1/2007 | Tsoukalis et al. |
| 7,167,755 | B2 | 1/2007 | Seeberger et al. |
| 7,167,920 | B2 | 1/2007 | Traversat |
| 7,171,277 | B2 | 1/2007 | Engleson et al. |
| 7,171,492 | B1 | 1/2007 | Borella et al. |
| 7,181,493 | B2 | 2/2007 | English et al. |
| 7,185,288 | B2 | 2/2007 | McKeever |
| 7,193,514 | B2 | 3/2007 | Ritson |
| 7,197,025 | B2 | 3/2007 | Chuah |
| 7,201,734 | B2 | 4/2007 | Hickle |
| 7,204,823 | B2 | 4/2007 | Estes et al. |
| 7,213,009 | B2 | 5/2007 | Pestotnik |
| 7,216,802 | B1 | 5/2007 | de la Huerga |
| 7,220,240 | B2 | 5/2007 | Struys et al. |
| 7,224,979 | B2 | 5/2007 | Singhal et al. |
| 7,229,430 | B2 | 6/2007 | Hickle et al. |
| 7,230,529 | B2 | 6/2007 | Ketcherside |
| 7,236,936 | B2 | 6/2007 | White et al. |
| 7,238,164 | B2 | 7/2007 | Childers et al. |
| 7,247,154 | B2 | 7/2007 | Hickle |
| 7,248,239 | B2 | 7/2007 | Dowling |
| 7,250,856 | B2 | 7/2007 | Havekost et al. |
| 7,255,683 | B2 | 8/2007 | Vanderveen et al. |
| 7,256,888 | B2 | 8/2007 | Staehr et al. |
| 7,258,534 | B2 | 8/2007 | Fathallah et al. |
| 7,263,213 | B2 | 8/2007 | Rowe |
| 7,267,664 | B2 | 9/2007 | Rizzo |
| 7,267,665 | B2 | 9/2007 | Steil et al. |
| 7,275,156 | B2 | 9/2007 | Balfanz et al. |
| 7,278,983 | B2 | 10/2007 | Ireland et al. |
| 7,289,815 | B2 | 10/2007 | Gfeller et al. |
| 7,289,948 | B1 | 10/2007 | Mohri |
| 7,293,107 | B1 | 11/2007 | Hanson et al. |
| 7,295,119 | B2 | 11/2007 | Rappaport et al. |
| 7,295,556 | B2 | 11/2007 | Roese et al. |
| 7,301,451 | B2 | 11/2007 | Hastings |
| 7,308,300 | B2 | 12/2007 | Toews et al. |
| 7,315,825 | B2 | 1/2008 | Rosenfeld et al. |
| 7,319,386 | B2 | 1/2008 | Collins, Jr. et al. |
| 7,324,000 | B2 | 1/2008 | Zittrain et al. |
| 7,327,705 | B2 | 2/2008 | Fletcher et al. |
| 7,343,224 | B2 | 3/2008 | DiGianfilippo et al. |
| 7,346,025 | B2 | 3/2008 | Bryson |
| 7,347,836 | B2 | 3/2008 | Peterson et al. |
| 7,354,420 | B2 | 4/2008 | Steil et al. |
| 7,369,897 | B2 | 5/2008 | Boveja et al. |
| 7,369,948 | B1 | 5/2008 | Ferenczi et al. |
| 7,383,088 | B2 | 6/2008 | Spinelli et al. |
| 7,384,410 | B2 | 6/2008 | Eggers et al. |
| 7,398,183 | B2 | 7/2008 | Holland et al. |
| 7,398,279 | B2 | 7/2008 | Muno, Jr. et al. |
| 7,399,277 | B2 | 7/2008 | Saidara et al. |
| 7,402,153 | B2 | 7/2008 | Steil et al. |
| 7,420,472 | B2 | 9/2008 | Tran |
| 7,432,807 | B2 | 10/2008 | Schmitt |
| 7,436,454 | B2 | 10/2008 | Yamaguchi et al. |
| 7,447,643 | B1 | 11/2008 | Olson |
| 7,454,314 | B2 | 11/2008 | Holland et al. |
| 7,457,804 | B2 | 11/2008 | Uber, III et al. |
| 7,464,040 | B2 | 12/2008 | Joao |
| 7,469,213 | B1 | 12/2008 | Rao |
| 7,471,994 | B2 | 12/2008 | Ford et al. |
| 7,483,756 | B2 | 1/2009 | Engleson et al. |
| 7,489,808 | B2 | 2/2009 | Gerder |

(56)                    References Cited

U.S. PATENT DOCUMENTS

| | | | |
|---|---|---|---|
| 7,490,021 | B2 | 2/2009 | Holland et al. |
| 7,490,048 | B2 | 2/2009 | Joao |
| 7,491,187 | B2 | 2/2009 | Van Den Berghe et al. |
| 7,519,905 | B2 | 4/2009 | Kougiouris et al. |
| 7,523,401 | B1 | 4/2009 | Aldridge |
| 7,524,304 | B2 | 4/2009 | Genosar |
| 7,551,078 | B2 | 6/2009 | Carlson |
| 7,559,321 | B2 | 7/2009 | Wermeling et al. |
| 7,565,197 | B2 | 7/2009 | Haulbrich et al. |
| 7,572,230 | B2 | 8/2009 | Neumann et al. |
| 7,578,802 | B2 | 8/2009 | Hickle |
| 7,621,009 | B2 | 11/2009 | Elhabashy |
| D606,533 | S | 12/2009 | De Jong et al. |
| 7,636,718 | B1 | 12/2009 | Steen et al. |
| 7,640,172 | B2 | 12/2009 | Kuth |
| 7,645,258 | B2 | 1/2010 | White et al. |
| 7,647,237 | B2 | 1/2010 | Malave et al. |
| 7,662,124 | B2 | 2/2010 | Duchon et al. |
| 7,668,731 | B2 | 2/2010 | Martucci et al. |
| 7,671,733 | B2 | 3/2010 | McNeal et al. |
| 7,678,071 | B2 | 3/2010 | Lebel et al. |
| 7,687,678 | B2 | 3/2010 | Jacobs |
| 7,697,994 | B2 | 4/2010 | VanDanacker et al. |
| 7,698,239 | B2 | 4/2010 | Lieuallen |
| 7,705,727 | B2 | 4/2010 | Pestotnik |
| 7,724,147 | B2 | 5/2010 | Brown et al. |
| 7,739,126 | B1 | 6/2010 | Cave |
| 7,746,218 | B2 | 6/2010 | Collins, Jr. |
| 7,766,873 | B2 | 8/2010 | Moberg et al. |
| 7,776,029 | B2 | 8/2010 | Whitehurst et al. |
| 7,776,031 | B2 | 8/2010 | Hartlaub et al. |
| 7,785,313 | B2 | 8/2010 | Mastrototaro |
| 7,788,369 | B2 | 8/2010 | McAllen et al. |
| 7,806,852 | B1 | 10/2010 | Jurson |
| 7,806,886 | B2 | 10/2010 | Kanderian, Jr. et al. |
| 7,826,981 | B2 | 11/2010 | Goode, Jr. et al. |
| 7,835,927 | B2 | 11/2010 | Schlotterbeck et al. |
| 7,836,314 | B2 | 11/2010 | Chieu |
| 7,856,276 | B2 | 12/2010 | Ripart et al. |
| 7,860,583 | B2 | 12/2010 | Condurso et al. |
| 7,864,771 | B2 | 1/2011 | Tavares et al. |
| 7,868,754 | B2 | 1/2011 | Salvat, Jr. |
| 7,871,394 | B2 | 1/2011 | Halbert et al. |
| 7,886,231 | B2 | 2/2011 | Hopermann et al. |
| 7,895,053 | B2 | 2/2011 | Holland et al. |
| 7,896,842 | B2 | 3/2011 | Palmroos et al. |
| 7,899,546 | B2 | 3/2011 | Sieracki et al. |
| 7,905,710 | B2 | 3/2011 | Wang et al. |
| 7,920,061 | B2 | 4/2011 | Klein et al. |
| 7,933,780 | B2 | 4/2011 | de la Huerga |
| 7,938,796 | B2 | 5/2011 | Moubayed |
| 7,945,452 | B2 | 5/2011 | Fathallah et al. |
| 7,974,714 | B2 | 7/2011 | Hoffberg |
| 7,976,508 | B2 | 7/2011 | Hoag |
| 7,996,241 | B2 | 8/2011 | Zak |
| 8,034,026 | B2 | 10/2011 | Grant |
| 8,038,593 | B2 | 10/2011 | Friedman et al. |
| 8,048,040 | B2 | 11/2011 | Kiani |
| 8,060,576 | B2 | 11/2011 | Chan et al. |
| 8,065,161 | B2 | 11/2011 | Howard et al. |
| 8,066,672 | B2 | 11/2011 | Mandro |
| 8,075,514 | B2 | 12/2011 | Butterfield et al. |
| 8,078,983 | B2 | 12/2011 | Davis et al. |
| 8,082,018 | B2 | 12/2011 | Duchon et al. |
| 8,082,312 | B2 | 12/2011 | Chan et al. |
| 8,095,692 | B2 | 1/2012 | Mehta et al. |
| 8,126,730 | B2 | 2/2012 | Dicks et al. |
| 8,147,448 | B2 | 4/2012 | Sundar et al. |
| 8,149,131 | B2 | 4/2012 | Blomquist |
| 8,169,914 | B2 | 5/2012 | Bajpai |
| 8,171,094 | B2 | 5/2012 | Chan et al. |
| 8,172,798 | B2 | 5/2012 | Hungerford et al. |
| 8,185,322 | B2 | 5/2012 | Schroeder et al. |
| 8,195,478 | B2 | 6/2012 | Petersen et al. |
| 8,206,350 | B2 | 6/2012 | Mann et al. |
| 8,219,413 | B2 | 7/2012 | Martinez et al. |
| 8,231,578 | B2 | 7/2012 | Fathallah et al. |
| 8,234,128 | B2 | 7/2012 | Martucci et al. |
| 8,267,892 | B2 | 9/2012 | Spencer et al. |
| 8,271,106 | B2 | 9/2012 | Wehba et al. |
| 8,287,495 | B2 | 10/2012 | Michaud et al. |
| 8,291,337 | B2 | 10/2012 | Gannin et al. |
| 8,298,184 | B2 | 10/2012 | DiPerna et al. |
| 8,312,272 | B1 | 11/2012 | Serenyl et al. |
| 8,352,290 | B2 | 1/2013 | Bartz et al. |
| 8,359,338 | B2 | 1/2013 | Butterfield et al. |
| 8,380,536 | B2 | 2/2013 | Howard et al. |
| 8,387,112 | B1 | 2/2013 | Ranjan et al. |
| 8,394,077 | B2 | 3/2013 | Jacobson et al. |
| 8,398,592 | B2 | 3/2013 | Leibner-Druska |
| 8,403,908 | B2 | 3/2013 | Jacobson et al. |
| 8,435,206 | B2 | 5/2013 | Evans et al. |
| 8,449,523 | B2 | 5/2013 | Brukalo et al. |
| 8,452,953 | B2 | 5/2013 | Buck et al. |
| 8,453,645 | B2 | 6/2013 | Figueiredo et al. |
| 8,472,630 | B2 | 6/2013 | Konrad et al. |
| 8,480,648 | B2 | 7/2013 | Burnett et al. |
| 8,486,019 | B2 | 7/2013 | White et al. |
| 8,489,427 | B2 | 7/2013 | Simpson et al. |
| 8,494,879 | B2 | 7/2013 | Davis et al. |
| 8,504,179 | B2 | 8/2013 | Blomquist |
| 8,517,990 | B2 | 8/2013 | Teel et al. |
| 8,518,021 | B2 | 8/2013 | Stewart et al. |
| 8,543,416 | B2 | 9/2013 | Palmroos et al. |
| 8,551,038 | B2 | 10/2013 | Tsoukalis et al. |
| 8,560,345 | B2 | 10/2013 | Wehba et al. |
| 8,567,681 | B2 | 10/2013 | Borges et al. |
| 8,577,692 | B2 | 11/2013 | Silkaitis et al. |
| 8,579,884 | B2 | 11/2013 | Lanier et al. |
| 8,626,530 | B1 | 1/2014 | Tran et al. |
| 8,655,676 | B2 | 2/2014 | Wehba et al. |
| 8,660,860 | B2 | 2/2014 | Wehba et al. |
| 8,662,388 | B2 | 3/2014 | Belkin |
| 8,666,769 | B2 | 3/2014 | Butler et al. |
| 8,667,293 | B2 | 3/2014 | Birtwhistle et al. |
| 8,687,811 | B2 | 4/2014 | Nierzwick et al. |
| 8,700,421 | B2 | 4/2014 | Feng et al. |
| 8,731,960 | B2 | 5/2014 | Butler et al. |
| 8,768,719 | B2 | 7/2014 | Wehba et al. |
| 8,771,251 | B2 | 7/2014 | Ruchti et al. |
| 8,777,894 | B2 | 7/2014 | Butterfield et al. |
| 8,777,895 | B2 | 7/2014 | Hsu et al. |
| 8,799,012 | B2 | 8/2014 | Butler et al. |
| 8,876,793 | B2 | 11/2014 | Ledford et al. |
| 8,886,316 | B1 | 11/2014 | Juels |
| 8,922,330 | B2 | 12/2014 | Moberg et al. |
| 8,936,565 | B2 | 1/2015 | Chawla |
| 8,945,043 | B2 | 2/2015 | Lee et al. |
| 8,952,794 | B2 | 2/2015 | Blomquist et al. |
| 8,959,617 | B2 | 2/2015 | Newlin et al. |
| 8,998,100 | B2 | 4/2015 | Halbert et al. |
| 9,026,370 | B2 | 5/2015 | Rubalcaba et al. |
| 9,069,887 | B2 | 6/2015 | Gupta et al. |
| 9,077,544 | B2 | 7/2015 | Baker et al. |
| 9,089,642 | B2 | 7/2015 | Murphy et al. |
| 9,114,217 | B2 | 8/2015 | Sur et al. |
| 9,123,077 | B2 | 9/2015 | Silkaitis et al. |
| 9,192,712 | B2 | 11/2015 | DeBelser et al. |
| 9,240,002 | B2 | 1/2016 | Hume et al. |
| 9,292,692 | B2 | 3/2016 | Wallrabenstein |
| 9,302,035 | B2 | 4/2016 | Marseille et al. |
| 9,313,154 | B1 | 4/2016 | Son |
| 9,381,296 | B2 | 7/2016 | Arrizza et al. |
| 9,393,362 | B2 | 7/2016 | Cozmi et al. |
| 9,430,655 | B1 | 8/2016 | Stockton et al. |
| 9,438,580 | B2 | 9/2016 | Kupper |
| 9,483,615 | B2 | 11/2016 | Roberts |
| 9,498,583 | B2 | 11/2016 | Sur et al. |
| 9,539,383 | B2 | 1/2017 | Kohlbrecher |
| 9,572,923 | B2 | 2/2017 | Howard et al. |
| 9,594,875 | B2 | 3/2017 | Arrizza et al. |
| 9,604,000 | B2 | 3/2017 | Wehba et al. |
| 9,641,432 | B2 | 5/2017 | Jha et al. |
| 9,649,431 | B2 | 5/2017 | Gray et al. |

(56) References Cited

U.S. PATENT DOCUMENTS

| | | |
|---|---|---|
| 9,662,436 B2 | 5/2017 | Belkin et al. |
| 9,690,909 B2 | 6/2017 | Stewart et al. |
| 9,707,341 B2 | 7/2017 | Dumas, III et al. |
| 9,717,845 B2 | 8/2017 | Istoc |
| 9,724,470 B2 | 8/2017 | Day et al. |
| 9,764,082 B2 | 9/2017 | Day et al. |
| 9,886,550 B2 | 2/2018 | Lee et al. |
| 9,943,269 B2 | 4/2018 | Muhsin et al. |
| 9,967,739 B2 | 5/2018 | Proennecke et al. |
| 9,971,871 B2 | 5/2018 | Arrizza et al. |
| 9,995,611 B2 | 6/2018 | Ruchti et al. |
| 10,022,498 B2 | 7/2018 | Ruchti et al. |
| 10,042,986 B2 | 8/2018 | Ruchti et al. |
| 10,046,112 B2 | 8/2018 | Oruklu et al. |
| 10,166,328 B2 | 1/2019 | Oruklu et al. |
| 10,173,008 B2 | 1/2019 | Simpson et al. |
| 10,188,849 B2 | 1/2019 | Fangrow |
| 10,233,179 B2 | 3/2019 | Ng et al. |
| 10,238,799 B2 | 3/2019 | Kohlbrecher |
| 10,238,801 B2 | 3/2019 | Wehba et al. |
| 10,242,060 B2 | 3/2019 | Butler et al. |
| 10,300,194 B2 | 5/2019 | Day et al. |
| 10,311,972 B2 | 6/2019 | Kohlbrecher et al. |
| 10,314,974 B2 | 6/2019 | Day et al. |
| 10,333,843 B2 | 6/2019 | Jha et al. |
| 10,341,866 B1 | 7/2019 | Spencer et al. |
| 10,409,995 B1 | 9/2019 | Wasiq |
| 10,430,761 B2 | 10/2019 | Hume et al. |
| 10,434,246 B2 | 10/2019 | Silkaitis et al. |
| 10,438,001 B1 | 10/2019 | Hariprasad |
| 10,452,842 B2 | 10/2019 | Dhondse |
| 10,453,157 B2 | 10/2019 | Kamen et al. |
| 10,463,788 B2 | 11/2019 | Day |
| 10,516,536 B2 | 12/2019 | Rommel |
| 10,617,815 B2 | 4/2020 | Day et al. |
| 10,646,651 B2 | 5/2020 | Day et al. |
| 10,681,207 B1 | 6/2020 | Johnson et al. |
| 10,692,595 B2 | 6/2020 | Xavier et al. |
| 10,728,262 B1 | 7/2020 | Vaswani |
| 10,740,436 B2 | 8/2020 | Moskal et al. |
| 10,741,280 B2 | 8/2020 | Xavier et al. |
| 10,757,219 B2 | 8/2020 | Moskal |
| 10,765,799 B2 | 9/2020 | Belkin et al. |
| 10,799,632 B2 | 10/2020 | Kohlbrecher |
| 10,812,380 B2 | 10/2020 | Jha et al. |
| 10,861,592 B2 | 12/2020 | Xavier et al. |
| 10,898,641 B2 | 1/2021 | Day et al. |
| 10,950,339 B2 | 3/2021 | Xavier et al. |
| 10,964,428 B2 | 3/2021 | Xavier et al. |
| 11,013,861 B2 | 5/2021 | Wehba et al. |
| 11,037,668 B2 | 6/2021 | Ruchti et al. |
| 11,052,193 B2 | 7/2021 | Day et al. |
| 11,139,058 B2 | 10/2021 | Xavier et al. |
| 11,151,290 B2 | 10/2021 | Karakoyunlu et al. |
| 11,152,108 B2 | 10/2021 | Xavier et al. |
| 11,152,109 B2 | 10/2021 | Xavier et al. |
| 11,152,110 B2 | 10/2021 | Xavier et al. |
| 11,194,810 B2 | 12/2021 | Butler et al. |
| 11,235,100 B2 | 2/2022 | Howard et al. |
| 11,289,183 B2 | 3/2022 | Kohlbrecher |
| 11,309,070 B2 | 4/2022 | Xavier et al. |
| 11,328,804 B2 | 5/2022 | Xavier et al. |
| 11,328,805 B2 | 5/2022 | Xavier et al. |
| 11,373,753 B2 | 6/2022 | Xavier et al. |
| 11,437,132 B2 | 9/2022 | Xavier et al. |
| 11,470,000 B2 | 10/2022 | Jha et al. |
| 11,483,402 B2 | 10/2022 | Xavier et al. |
| 11,483,403 B2 | 10/2022 | Xavier et al. |
| 11,501,877 B2 | 11/2022 | Kohlbrecher et al. |
| 11,571,508 B2 | 2/2023 | Jacobson et al. |
| 11,574,721 B2 | 2/2023 | Kohlbrecher |
| 11,574,737 B2 | 2/2023 | Dharwad et al. |
| 11,587,669 B2 | 2/2023 | Xavier et al. |
| 11,590,057 B2 | 2/2023 | Tagliamento et al. |
| 11,594,326 B2 | 2/2023 | Xavier et al. |
| 11,605,468 B2 | 3/2023 | Jacobson et al. |
| 11,626,205 B2 | 4/2023 | Arrizza et al. |
| 11,628,246 B2 | 4/2023 | Day et al. |
| 11,628,254 B2 | 4/2023 | Day et al. |
| 11,654,237 B2 | 5/2023 | Wehba et al. |
| 11,670,416 B2 | 6/2023 | Xavier et al. |
| 11,763,927 B2 | 9/2023 | Ruchti et al. |
| 11,783,935 B2 | 10/2023 | Xavier et al. |
| 11,881,297 B2 | 1/2024 | Xavier et al. |
| 11,923,076 B2 | 3/2024 | Xavier et al. |
| 11,986,623 B2 | 5/2024 | Jacobson et al. |
| 11,996,188 B2 | 5/2024 | Arrizza et al. |
| 12,002,562 B2 | 6/2024 | Kohlbrecher |
| 12,036,390 B2 | 7/2024 | Wehba et al. |
| 12,040,068 B2 | 7/2024 | Xavier et al. |
| 12,042,623 B2 | 7/2024 | Day et al. |
| 12,042,631 B2 | 7/2024 | Day et al. |
| 12,046,361 B2 | 7/2024 | Xavier et al. |
| 12,047,292 B2 | 7/2024 | Jha et al. |
| 2001/0016056 A1 | 8/2001 | Westphal et al. |
| 2001/0029178 A1 | 10/2001 | Criss et al. |
| 2001/0031944 A1 | 10/2001 | Peterson et al. |
| 2001/0032099 A1 | 10/2001 | Joao |
| 2001/0037060 A1 | 11/2001 | Thompson et al. |
| 2001/0044731 A1 | 11/2001 | Coffman et al. |
| 2001/0048027 A1 | 12/2001 | Walsh |
| 2001/0051787 A1 | 12/2001 | Haller et al. |
| 2001/0056358 A1 | 12/2001 | Dulong et al. |
| 2002/0010595 A1 | 1/2002 | Kapp |
| 2002/0013551 A1 | 1/2002 | Zaitsu et al. |
| 2002/0013723 A1 | 1/2002 | Mise |
| 2002/0015018 A1 | 2/2002 | Shimazu et al. |
| 2002/0019584 A1 | 2/2002 | Schulze et al. |
| 2002/0021700 A1 | 2/2002 | Hata et al. |
| 2002/0026103 A1 | 2/2002 | Norris et al. |
| 2002/0029776 A1 | 3/2002 | Blomquist |
| 2002/0032583 A1 | 3/2002 | Joao |
| 2002/0040208 A1 | 4/2002 | Flaherty et al. |
| 2002/0040282 A1 | 4/2002 | Bailey et al. |
| 2002/0044043 A1 | 4/2002 | Chaco et al. |
| 2002/0044059 A1 | 4/2002 | Reeder et al. |
| 2002/0082728 A1 | 6/2002 | Mueller et al. |
| 2002/0087115 A1 | 7/2002 | Hartlaub |
| 2002/0087116 A1 | 7/2002 | Hartlaub |
| 2002/0095486 A1 | 7/2002 | Bahl |
| 2002/0103675 A1 | 8/2002 | Vanelli |
| 2002/0123905 A1 | 9/2002 | Goodroe et al. |
| 2002/0143580 A1 | 10/2002 | Bristol et al. |
| 2002/0152239 A1 | 10/2002 | Bautista-Lloyd et al. |
| 2002/0154600 A1 | 10/2002 | Ido et al. |
| 2002/0173702 A1 | 11/2002 | Lebel et al. |
| 2002/0173875 A1 | 11/2002 | Wallace et al. |
| 2002/0193679 A1 | 12/2002 | Malave et al. |
| 2002/0194329 A1 | 12/2002 | Alling |
| 2003/0009244 A1 | 1/2003 | Engleson |
| 2003/0013959 A1 | 1/2003 | Grunwald et al. |
| 2003/0014222 A1 | 1/2003 | Klass et al. |
| 2003/0014817 A1 | 1/2003 | Gallant et al. |
| 2003/0025602 A1 | 2/2003 | Medema et al. |
| 2003/0028082 A1 | 2/2003 | Thompson |
| 2003/0036683 A1 | 2/2003 | Kehr et al. |
| 2003/0036744 A1 | 2/2003 | Struys et al. |
| 2003/0047126 A1 | 3/2003 | Tomaschko |
| 2003/0047600 A1 | 3/2003 | Nakanishi et al. |
| 2003/0050621 A1 | 3/2003 | Lebel et al. |
| 2003/0059750 A1 | 3/2003 | Bindler et al. |
| 2003/0060688 A1 | 3/2003 | Ciarniello et al. |
| 2003/0069963 A1 | 4/2003 | Jayant et al. |
| 2003/0079746 A1 | 5/2003 | Hickle |
| 2003/0097529 A1 | 5/2003 | Arimilli et al. |
| 2003/0104982 A1 | 6/2003 | Wittmann et al. |
| 2003/0105389 A1 | 6/2003 | Noonan et al. |
| 2003/0106553 A1 | 6/2003 | Vanderveen |
| 2003/0115358 A1 | 6/2003 | Yun |
| 2003/0120384 A1 | 6/2003 | Haitin et al. |
| 2003/0125662 A1 | 7/2003 | Bui |
| 2003/0130616 A1 | 7/2003 | Steil |
| 2003/0135087 A1 | 7/2003 | Hickle et al. |
| 2003/0139701 A1 | 7/2003 | White et al. |

(56)                    References Cited

U.S. PATENT DOCUMENTS

| | | |
|---|---|---|
| 2003/0140928 A1 | 7/2003 | Bui et al. |
| 2003/0140929 A1 | 7/2003 | Wilkes et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158749 A1 | 8/2003 | Olchanski et al. |
| 2003/0187338 A1 | 10/2003 | Say et al. |
| 2003/0200116 A1 | 10/2003 | Forrester |
| 2003/0204416 A1 | 10/2003 | Acharya |
| 2003/0204781 A1 | 10/2003 | Peebles et al. |
| 2003/0212364 A1 | 11/2003 | Mann et al. |
| 2003/0212379 A1 | 11/2003 | Bylund et al. |
| 2003/0212821 A1 | 11/2003 | Gillies et al. |
| 2003/0216831 A1 | 11/2003 | Hart et al. |
| 2003/0217962 A1 | 11/2003 | Childers et al. |
| 2004/0008123 A1 | 1/2004 | Carrender et al. |
| 2004/0010786 A1 | 1/2004 | Cool et al. |
| 2004/0015132 A1 | 1/2004 | Brown |
| 2004/0019464 A1 | 1/2004 | Martucci et al. |
| 2004/0019607 A1 | 1/2004 | Moubayed et al. |
| 2004/0030323 A1 | 2/2004 | Ullestad et al. |
| 2004/0039257 A1 | 2/2004 | Hickle |
| 2004/0057226 A1 | 3/2004 | Berthou et al. |
| 2004/0064341 A1 | 4/2004 | Langan et al. |
| 2004/0064342 A1 | 4/2004 | Browne et al. |
| 2004/0064435 A1 | 4/2004 | Moubayed et al. |
| 2004/0073161 A1 | 4/2004 | Tachibana |
| 2004/0073811 A1 | 4/2004 | Sanin |
| 2004/0077934 A1 | 4/2004 | Massad |
| 2004/0078231 A1 | 4/2004 | Wilkes et al. |
| 2004/0078236 A1 | 4/2004 | Stoodley et al. |
| 2004/0085186 A1 | 5/2004 | Eveland et al. |
| 2004/0104271 A1 | 6/2004 | Martucci et al. |
| 2004/0122530 A1 | 6/2004 | Hansen |
| 2004/0128162 A1 | 7/2004 | Schlotterbeck et al. |
| 2004/0128163 A1 | 7/2004 | Goodman et al. |
| 2004/0133441 A1 | 7/2004 | Brady et al. |
| 2004/0139004 A1 | 7/2004 | Cohen et al. |
| 2004/0145480 A1 | 7/2004 | Despotis |
| 2004/0147034 A1 | 7/2004 | Gore et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0176980 A1 | 9/2004 | Bulitta et al. |
| 2004/0176984 A1 | 9/2004 | White et al. |
| 2004/0181314 A1 | 9/2004 | Zaleski |
| 2004/0189708 A1 | 9/2004 | Larcheveque et al. |
| 2004/0193325 A1 | 9/2004 | Bonderud |
| 2004/0193328 A1 | 9/2004 | Butterfield et al. |
| 2004/0204673 A1 | 10/2004 | Flaherty et al. |
| 2004/0215278 A1 | 10/2004 | Stegink et al. |
| 2004/0220517 A1 | 11/2004 | Starkweather et al. |
| 2004/0225252 A1 | 11/2004 | Gillespie et al. |
| 2004/0236240 A1 | 11/2004 | Kraus et al. |
| 2004/0243438 A1 | 12/2004 | Mintz |
| 2004/0254434 A1 | 12/2004 | Goodnow et al. |
| 2005/0010269 A1 | 1/2005 | Lebel et al. |
| 2005/0020886 A1 | 1/2005 | Hutchinson et al. |
| 2005/0021006 A1 | 1/2005 | Tonnies |
| 2005/0027560 A1 | 2/2005 | Cook |
| 2005/0027567 A1 | 2/2005 | Taha |
| 2005/0038311 A1 | 2/2005 | Kuth |
| 2005/0038669 A1 | 2/2005 | Sachdeva et al. |
| 2005/0038680 A1 | 2/2005 | McMahon |
| 2005/0040226 A1 | 2/2005 | Al-Sheikh |
| 2005/0043620 A1 | 2/2005 | Fallows et al. |
| 2005/0049910 A1 | 3/2005 | Lancaster et al. |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0065817 A1 | 3/2005 | Mihai et al. |
| 2005/0075544 A1 | 4/2005 | Shapiro et al. |
| 2005/0080801 A1 | 4/2005 | Kothandaraman et al. |
| 2005/0086071 A1 | 4/2005 | Fox, Jr. et al. |
| 2005/0086072 A1 | 4/2005 | Fox |
| 2005/0088704 A1 | 4/2005 | Vaschillo et al. |
| 2005/0090808 A1 | 4/2005 | Malave et al. |
| 2005/0099624 A1 | 5/2005 | Staehr |
| 2005/0102162 A1 | 5/2005 | Blumenfeld |
| 2005/0102165 A1 | 5/2005 | Oshita et al. |
| 2005/0102167 A1 | 5/2005 | Kapoor |
| 2005/0102669 A1 | 5/2005 | Marney et al. |
| 2005/0107923 A1 | 5/2005 | Vanderveen |
| 2005/0108057 A1 | 5/2005 | Cohen et al. |
| 2005/0117529 A1 | 6/2005 | Ramos-Escano |
| 2005/0119788 A1 | 6/2005 | Engleson et al. |
| 2005/0119914 A1 | 6/2005 | Batch |
| 2005/0131739 A1 | 6/2005 | Rabinowitz et al. |
| 2005/0135306 A1 | 6/2005 | McAllen et al. |
| 2005/0137522 A1 | 6/2005 | Aoki |
| 2005/0137573 A1 | 6/2005 | Mclaughlin |
| 2005/0138428 A1 | 6/2005 | McAllen et al. |
| 2005/0154769 A1 | 7/2005 | Eckart et al. |
| 2005/0160057 A1 | 7/2005 | Wefers et al. |
| 2005/0171503 A1 | 8/2005 | Van Den Berghe et al. |
| 2005/0171815 A1 | 8/2005 | Vanderveen |
| 2005/0177096 A1 | 8/2005 | Bollish et al. |
| 2005/0177395 A1 | 8/2005 | Blomquist |
| 2005/0182306 A1 | 8/2005 | Sloan |
| 2005/0182355 A1 | 8/2005 | Bui |
| 2005/0187950 A1 | 8/2005 | Parker |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0210037 A1 | 9/2005 | Wefers et al. |
| 2005/0216479 A1 | 9/2005 | Wefers et al. |
| 2005/0216480 A1 | 9/2005 | Wefers et al. |
| 2005/0223045 A1 | 10/2005 | Funahashi et al. |
| 2005/0224083 A1 | 10/2005 | Crass |
| 2005/0234746 A1 | 10/2005 | Funahashi |
| 2005/0240305 A1 | 10/2005 | Bogash et al. |
| 2005/0246416 A1 | 11/2005 | Blomquist |
| 2005/0251418 A1 | 11/2005 | Fox, Jr. et al. |
| 2005/0261660 A1 | 11/2005 | Choi |
| 2005/0273059 A1 | 12/2005 | Mernoe et al. |
| 2005/0273367 A1 | 12/2005 | Nourie et al. |
| 2005/0277873 A1 | 12/2005 | Stewart et al. |
| 2005/0277890 A1 | 12/2005 | Stewart et al. |
| 2005/0278194 A1 | 12/2005 | Holland et al. |
| 2006/0004772 A1 | 1/2006 | Hagan et al. |
| 2006/0009727 A1 | 1/2006 | O'Mahony et al. |
| 2006/0009734 A1 | 1/2006 | Martin |
| 2006/0010098 A1 | 1/2006 | Goodnow et al. |
| 2006/0042139 A1 | 3/2006 | Mendes |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0074633 A1 | 4/2006 | Mahesh et al. |
| 2006/0074920 A1 | 4/2006 | Wefers et al. |
| 2006/0079831 A1 | 4/2006 | Gilbert |
| 2006/0089539 A1 | 4/2006 | Miodownik et al. |
| 2006/0089854 A1 | 4/2006 | Holland et al. |
| 2006/0089855 A1 | 4/2006 | Holland et al. |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0111943 A1 | 5/2006 | Wu |
| 2006/0116904 A1 | 6/2006 | Brem |
| 2006/0116907 A1 | 6/2006 | Rhodes et al. |
| 2006/0122481 A1 | 6/2006 | Sievenpiper et al. |
| 2006/0122867 A1 | 6/2006 | Eggers et al. |
| 2006/0129140 A1 | 6/2006 | Todd et al. |
| 2006/0129429 A1 | 6/2006 | Moubayed et al. |
| 2006/0129434 A1 | 6/2006 | Smitherman et al. |
| 2006/0129435 A1 | 6/2006 | Smitherman et al. |
| 2006/0136266 A1 | 6/2006 | Tarassenko et al. |
| 2006/0136271 A1 | 6/2006 | Eggers et al. |
| 2006/0143051 A1 | 6/2006 | Eggers et al. |
| 2006/0173260 A1 | 8/2006 | Gaoni et al. |

(56)                    References Cited

U.S. PATENT DOCUMENTS

| | | |
|---|---|---|
| 2006/0173406 A1 | 8/2006 | Hayes et al. |
| 2006/0173715 A1 | 8/2006 | Wang et al. |
| 2006/0173927 A1 | 8/2006 | Beyer et al. |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224141 A1 | 10/2006 | Rush et al. |
| 2006/0229918 A1 | 10/2006 | Fotsch et al. |
| 2006/0236373 A1 | 10/2006 | Graves et al. |
| 2006/0247606 A1 | 11/2006 | Batch |
| 2006/0253554 A1 | 11/2006 | Uwais |
| 2006/0258985 A1 | 11/2006 | Russell |
| 2006/0259327 A1 | 11/2006 | Hoag |
| 2006/0264895 A1 | 11/2006 | Flanders |
| 2006/0267753 A1 | 11/2006 | Hussey et al. |
| 2006/0268710 A1 | 11/2006 | Appanna et al. |
| 2006/0270971 A1 | 11/2006 | Gelfand et al. |
| 2006/0277206 A1 | 12/2006 | Bailey et al. |
| 2006/0287885 A1 | 12/2006 | Frick |
| 2007/0015972 A1 | 1/2007 | Wang et al. |
| 2007/0016443 A1 | 1/2007 | Wachman et al. |
| 2007/0021715 A1 | 1/2007 | Kohlbrenner et al. |
| 2007/0027506 A1 | 2/2007 | Stender et al. |
| 2007/0060796 A1 | 3/2007 | Kim |
| 2007/0060870 A1 | 3/2007 | Tolle et al. |
| 2007/0060871 A1 | 3/2007 | Istoc |
| 2007/0061393 A1 | 3/2007 | Moore |
| 2007/0065363 A1 | 3/2007 | Dalal et al. |
| 2007/0073419 A1 | 3/2007 | Sesay |
| 2007/0073822 A1 | 3/2007 | Bennett et al. |
| 2007/0078314 A1 | 4/2007 | Grounsell |
| 2007/0083870 A1 | 4/2007 | Kanakogi |
| 2007/0088333 A1 | 4/2007 | Levin et al. |
| 2007/0093786 A1 | 4/2007 | Goldsmith et al. |
| 2007/0100665 A1 | 5/2007 | Brown |
| 2007/0100667 A1 | 5/2007 | Bardy |
| 2007/0106126 A1 | 5/2007 | Mannheimer et al. |
| 2007/0112298 A1 | 5/2007 | Mueller et al. |
| 2007/0116037 A1 | 5/2007 | Moore |
| 2007/0118405 A1 | 5/2007 | Campbell et al. |
| 2007/0135866 A1 | 6/2007 | Baker et al. |
| 2007/0136098 A1 | 6/2007 | Smythe et al. |
| 2007/0142822 A1 | 6/2007 | Remde |
| 2007/0156282 A1 | 7/2007 | Dunn |
| 2007/0156452 A1 | 7/2007 | Batch |
| 2007/0169008 A1 | 7/2007 | Varanasi et al. |
| 2007/0179448 A1 | 8/2007 | Lim et al. |
| 2007/0186923 A1 | 8/2007 | Poutiatine et al. |
| 2007/0191817 A1 | 8/2007 | Martin |
| 2007/0191973 A1 | 8/2007 | Holzbauer et al. |
| 2007/0213657 A1 | 9/2007 | Jennewine et al. |
| 2007/0213684 A1 | 9/2007 | Hickle et al. |
| 2007/0214003 A1 | 9/2007 | Holland et al. |
| 2007/0215545 A1 | 9/2007 | Bissler et al. |
| 2007/0232867 A1 | 10/2007 | Hansmann |
| 2007/0233035 A1 | 10/2007 | Wehba et al. |
| 2007/0233049 A1 | 10/2007 | Wehba et al. |
| 2007/0233206 A1 | 10/2007 | Frikart |
| 2007/0240215 A1 | 10/2007 | Flores |
| 2007/0251835 A1 | 11/2007 | Mehta et al. |
| 2007/0253021 A1 | 11/2007 | Mehta et al. |
| 2007/0254593 A1 | 11/2007 | Jollota et al. |
| 2007/0255125 A1 | 11/2007 | Moberg et al. |
| 2007/0257788 A1 | 11/2007 | Carlson |
| 2007/0258395 A1 | 11/2007 | Jollota et al. |
| 2007/0299687 A1 | 12/2007 | Palmer et al. |
| 2007/0299695 A1 | 12/2007 | Jung et al. |
| 2008/0001771 A1 | 1/2008 | Faoro et al. |
| 2008/0004904 A1 | 1/2008 | Tran |
| 2008/0009684 A1 | 1/2008 | Corsetti et al. |
| 2008/0033361 A1 | 2/2008 | Evans et al. |
| 2008/0033966 A1 | 2/2008 | Wahl |
| 2008/0034323 A1 | 2/2008 | Blomquist |
| 2008/0041942 A1 | 2/2008 | Aissa |
| 2008/0052704 A1 | 2/2008 | Wysocki |
| 2008/0065007 A1 | 3/2008 | Peterson et al. |
| 2008/0065417 A1 | 3/2008 | Jung et al. |
| 2008/0071217 A1 | 3/2008 | Moubayed et al. |
| 2008/0071251 A1 | 3/2008 | Moubayed et al. |
| 2008/0086088 A1 | 4/2008 | Malcolm |
| 2008/0091466 A1 | 4/2008 | Butler et al. |
| 2008/0095339 A1 | 4/2008 | Elliott |
| 2008/0097289 A1 | 4/2008 | Steil et al. |
| 2008/0097552 A1 | 4/2008 | Dicks et al. |
| 2008/0126969 A1 | 5/2008 | Blomquist |
| 2008/0139907 A1 | 6/2008 | Rao et al. |
| 2008/0148047 A1 | 6/2008 | Appenzeller et al. |
| 2008/0149117 A1 | 6/2008 | Raghuram |
| 2008/0154177 A1 | 6/2008 | Moubayed et al. |
| 2008/0172337 A1 | 7/2008 | Banfield et al. |
| 2008/0184219 A1 | 7/2008 | Matsumoto |
| 2008/0188796 A1 | 8/2008 | Steil et al. |
| 2008/0214919 A1 | 9/2008 | Harmon et al. |
| 2008/0246748 A1 | 10/2008 | Cassidy et al. |
| 2008/0256305 A1 | 10/2008 | Kwon |
| 2008/0259926 A1 | 10/2008 | Tavares et al. |
| 2008/0262469 A1 | 10/2008 | Bristol et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2008/0301298 A1 | 12/2008 | Bernardi et al. |
| 2008/0320387 A1 | 12/2008 | Sasaki et al. |
| 2008/0320466 A1 | 12/2008 | Dias |
| 2009/0003554 A1 | 1/2009 | Katis et al. |
| 2009/0005703 A1 | 1/2009 | Fasciano |
| 2009/0005728 A1 | 1/2009 | Weinert et al. |
| 2009/0006061 A1 | 1/2009 | Thukral et al. |
| 2009/0006129 A1 | 1/2009 | Thukral |
| 2009/0006133 A1 | 1/2009 | Weinert |
| 2009/0018495 A1 | 1/2009 | Panduro |
| 2009/0036750 A1 | 2/2009 | Weinstein et al. |
| 2009/0051560 A1 | 2/2009 | Manning et al. |
| 2009/0054743 A1 | 2/2009 | Stewart |
| 2009/0054754 A1 | 2/2009 | McMahon et al. |
| 2009/0057399 A1 | 3/2009 | Sajkowsky |
| 2009/0063187 A1 | 3/2009 | Johnson et al. |
| 2009/0069785 A1 | 3/2009 | Miller et al. |
| 2009/0099867 A1 | 4/2009 | Newman |
| 2009/0135196 A1 | 5/2009 | Holland et al. |
| 2009/0143662 A1 | 6/2009 | Estes et al. |
| 2009/0149743 A1 | 6/2009 | Barron et al. |
| 2009/0150174 A1 | 6/2009 | Buck et al. |
| 2009/0150439 A1 | 6/2009 | Gejdos et al. |
| 2009/0150878 A1 | 6/2009 | Pathak et al. |
| 2009/0157695 A1 | 6/2009 | Roberts |
| 2009/0158274 A1 | 6/2009 | Roberts |
| 2009/0177146 A1 | 7/2009 | Nesbitt et al. |
| 2009/0177769 A1 | 7/2009 | Roberts |
| 2009/0183147 A1 | 7/2009 | Davis et al. |
| 2009/0209938 A1 | 8/2009 | Aalto-Setala |
| 2009/0210250 A1 | 8/2009 | Prax et al. |
| 2009/0221890 A1 | 9/2009 | Saffer et al. |
| 2009/0231249 A1 | 9/2009 | Wang et al. |
| 2009/0270833 A1 | 10/2009 | DeBelser |
| 2009/0275886 A1 | 11/2009 | Blomquist et al. |
| 2009/0275896 A1 | 11/2009 | Kamen et al. |
| 2009/0284691 A1 | 11/2009 | Marhefka et al. |
| 2009/0292340 A1 | 11/2009 | Mass et al. |
| 2009/0306573 A1 | 12/2009 | Gagner et al. |
| 2009/0326340 A1 | 12/2009 | Wang |
| 2009/0326516 A1 | 12/2009 | Bangera et al. |
| 2010/0008377 A1 | 1/2010 | Hasti et al. |
| 2010/0022988 A1 | 1/2010 | Wochner |
| 2010/0036310 A1 | 2/2010 | Hillman |
| 2010/0056992 A1 | 3/2010 | Hayter |
| 2010/0083060 A1 | 4/2010 | Rahman |
| 2010/0095229 A1 | 4/2010 | Dixon et al. |
| 2010/0121170 A1 | 5/2010 | Rule |
| 2010/0121246 A1 | 5/2010 | Peters et al. |
| 2010/0121415 A1 | 5/2010 | Skelton et al. |
| 2010/0121654 A1 | 5/2010 | Portnoy et al. |

(56)　　　　　　References Cited

U.S. PATENT DOCUMENTS

| | | |
|---|---|---|
| 2010/0121752 A1 | 5/2010 | Banigan et al. |
| 2010/0130933 A1 | 5/2010 | Holland et al. |
| 2010/0131434 A1 | 5/2010 | Magent et al. |
| 2010/0138523 A1 | 6/2010 | Umess et al. |
| 2010/0146137 A1 | 6/2010 | Wu et al. |
| 2010/0156633 A1 | 6/2010 | Buck et al. |
| 2010/0160854 A1 | 6/2010 | Gauthier |
| 2010/0160860 A1 | 6/2010 | Celentano et al. |
| 2010/0174266 A1 | 7/2010 | Estes |
| 2010/0191525 A1 | 7/2010 | Rabenko et al. |
| 2010/0198034 A1 | 8/2010 | Thomas et al. |
| 2010/0198196 A1 | 8/2010 | Wei |
| 2010/0200506 A1 | 8/2010 | Ware et al. |
| 2010/0209268 A1 | 8/2010 | Davis |
| 2010/0212675 A1 | 8/2010 | Walling et al. |
| 2010/0217621 A1 | 8/2010 | Schoenberg |
| 2010/0234708 A1 | 9/2010 | Buck et al. |
| 2010/0250732 A1 | 9/2010 | Bucknell |
| 2010/0271479 A1 | 10/2010 | Heydlauf |
| 2010/0273738 A1 | 10/2010 | Valcke et al. |
| 2010/0274218 A1 | 10/2010 | Yodfat et al. |
| 2010/0280486 A1 | 11/2010 | Khair et al. |
| 2010/0292634 A1 | 11/2010 | Kircher |
| 2010/0298765 A1 | 11/2010 | Budiman et al. |
| 2010/0318025 A1 | 12/2010 | John |
| 2011/0001605 A1 | 1/2011 | Kiani et al. |
| 2011/0021898 A1 | 1/2011 | Wei et al. |
| 2011/0028885 A1* | 2/2011 | Eggers .................. G16H 40/67 |
| | | 235/375 |
| 2011/0040158 A1 | 2/2011 | Katz et al. |
| 2011/0060758 A1 | 3/2011 | Schlotterbeck et al. |
| 2011/0071844 A1 | 3/2011 | Cannon et al. |
| 2011/0072379 A1 | 3/2011 | Gannon |
| 2011/0078253 A1 | 3/2011 | Chan et al. |
| 2011/0078608 A1 | 3/2011 | Gannon et al. |
| 2011/0093284 A1 | 4/2011 | Dicks et al. |
| 2011/0099313 A1 | 4/2011 | Bolanowski |
| 2011/0106318 A1 | 5/2011 | Ledford et al. |
| 2011/0125095 A1 | 5/2011 | Lebel et al. |
| 2011/0138185 A1 | 6/2011 | Ju et al. |
| 2011/0166628 A1 | 7/2011 | Jain |
| 2011/0175728 A1 | 7/2011 | Baker, Jr. |
| 2011/0178462 A1 | 7/2011 | Moberg et al. |
| 2011/0185010 A1 | 7/2011 | Shatsky et al. |
| 2011/0196748 A1 | 8/2011 | Caron et al. |
| 2011/0231216 A1 | 9/2011 | Fyke et al. |
| 2011/0252230 A1 | 10/2011 | Segre et al. |
| 2011/0257496 A1 | 10/2011 | Terashima et al. |
| 2011/0257798 A1 | 10/2011 | Ali et al. |
| 2011/0259954 A1 | 10/2011 | Bartz et al. |
| 2011/0264043 A1 | 10/2011 | Kotnick et al. |
| 2011/0264044 A1 | 10/2011 | Bartz et al. |
| 2011/0266221 A1 | 11/2011 | Ware et al. |
| 2011/0270045 A1 | 11/2011 | Lebel et al. |
| 2011/0275904 A1 | 11/2011 | Lebel et al. |
| 2011/0286457 A1 | 11/2011 | Ee |
| 2011/0289314 A1 | 11/2011 | Whitcomb |
| 2011/0289497 A1 | 11/2011 | Kiaie et al. |
| 2011/0295196 A1 | 12/2011 | Chazot et al. |
| 2011/0295341 A1 | 12/2011 | Estes et al. |
| 2011/0296051 A1 | 12/2011 | Vange |
| 2011/0296411 A1 | 12/2011 | Tang et al. |
| 2011/0313789 A1 | 12/2011 | Karmen et al. |
| 2011/0319813 A1 | 12/2011 | Kamen et al. |
| 2011/0320049 A1 | 12/2011 | Chossat et al. |
| 2012/0005680 A1 | 1/2012 | Dolby et al. |
| 2012/0011253 A1 | 1/2012 | Friedman et al. |
| 2012/0016305 A1 | 1/2012 | Jollota |
| 2012/0029941 A1 | 2/2012 | Malave et al. |
| 2012/0036102 A1 | 2/2012 | Fletcher et al. |
| 2012/0036550 A1 | 2/2012 | Rodriguez |
| 2012/0066501 A1 | 3/2012 | Xiong |
| 2012/0070045 A1 | 3/2012 | Vesper et al. |
| 2012/0079084 A1 | 3/2012 | Forssell et al. |
| 2012/0095437 A1 | 4/2012 | Hemmerling |
| 2012/0112903 A1 | 5/2012 | Kaib et al. |
| 2012/0130198 A1 | 5/2012 | Beaule |
| 2012/0143116 A1 | 6/2012 | Ware et al. |
| 2012/0150556 A1 | 6/2012 | Galasso et al. |
| 2012/0157920 A1 | 6/2012 | Flachbart et al. |
| 2012/0179135 A1 | 7/2012 | Rinehart et al. |
| 2012/0179136 A1 | 7/2012 | Rinehart et al. |
| 2012/0185267 A1 | 7/2012 | Kamen et al. |
| 2012/0203177 A1 | 8/2012 | Lanier |
| 2012/0245554 A1 | 9/2012 | Kawamura |
| 2012/0259978 A1 | 10/2012 | Petersen et al. |
| 2012/0260012 A1 | 10/2012 | Gao-Saari et al. |
| 2012/0277716 A1 | 11/2012 | Ali et al. |
| 2012/0283630 A1 | 11/2012 | Lee et al. |
| 2012/0284734 A1 | 11/2012 | McQuaid et al. |
| 2012/0323212 A1 | 12/2012 | Murphy |
| 2012/0330380 A1 | 12/2012 | Corndorf |
| 2013/0006666 A1 | 1/2013 | Schneider |
| 2013/0006702 A1 | 1/2013 | Wu |
| 2013/0012877 A1 | 1/2013 | Debelser et al. |
| 2013/0012879 A1 | 1/2013 | Debelser et al. |
| 2013/0012880 A1 | 1/2013 | Blomquist |
| 2013/0015980 A1 | 1/2013 | Evans et al. |
| 2013/0036403 A1 | 2/2013 | Geist |
| 2013/0036412 A1 | 2/2013 | Birtwhistle et al. |
| 2013/0066265 A1 | 3/2013 | Grant |
| 2013/0072872 A1 | 3/2013 | Yodfat et al. |
| 2013/0091350 A1 | 4/2013 | Gluck |
| 2013/0096444 A1 | 4/2013 | Condurso et al. |
| 2013/0096648 A1 | 4/2013 | Benson |
| 2013/0102963 A1 | 4/2013 | Marsh et al. |
| 2013/0114594 A1 | 5/2013 | Van Zijst |
| 2013/0116578 A1 | 5/2013 | An |
| 2013/0133083 A1 | 5/2013 | Kurumai |
| 2013/0138452 A1 | 5/2013 | Cork et al. |
| 2013/0150824 A1 | 6/2013 | Estes et al. |
| 2013/0167245 A1 | 6/2013 | Birtwhistle et al. |
| 2013/0173473 A1 | 7/2013 | Birtwhistle et al. |
| 2013/0191770 A1 | 7/2013 | Bartz et al. |
| 2013/0204188 A1 | 8/2013 | Kamen et al. |
| 2013/0218080 A1 | 8/2013 | Peterfreund et al. |
| 2013/0274669 A1 | 10/2013 | Stempfle et al. |
| 2013/0275539 A1 | 10/2013 | Gross et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0317753 A1 | 11/2013 | Kamen et al. |
| 2013/0346108 A1 | 12/2013 | Kamen et al. |
| 2014/0025392 A1 | 1/2014 | Chandrasenan |
| 2014/0108783 A1 | 4/2014 | Suzuki |
| 2014/0142540 A1 | 5/2014 | Imhof |
| 2014/0142963 A1 | 5/2014 | Hill et al. |
| 2014/0163517 A1 | 6/2014 | Finan et al. |
| 2014/0172994 A1 | 6/2014 | Raumann et al. |
| 2014/0180711 A1 | 6/2014 | Kamen et al. |
| 2014/0197950 A1 | 7/2014 | Shupp et al. |
| 2014/0215490 A1 | 7/2014 | Mathur et al. |
| 2014/0257251 A1 | 9/2014 | Bush et al. |
| 2014/0266790 A1 | 9/2014 | Al-Ali et al. |
| 2014/0266794 A1 | 9/2014 | Brown et al. |
| 2014/0269643 A1 | 9/2014 | Sun |
| 2014/0276571 A1 | 9/2014 | Ludolph |
| 2014/0280522 A1 | 9/2014 | Watte |
| 2014/0294177 A1 | 10/2014 | Shastry et al. |
| 2014/0297329 A1 | 10/2014 | Rock |
| 2014/0316819 A1 | 10/2014 | Dunsirn et al. |
| 2014/0318639 A1 | 10/2014 | Peret et al. |
| 2014/0366878 A1 | 12/2014 | Baron |
| 2014/0371543 A1 | 12/2014 | Steinhauer et al. |
| 2015/0005935 A1 | 1/2015 | Bae et al. |
| 2015/0006907 A1 | 1/2015 | Brouwer et al. |
| 2015/0045729 A1 | 2/2015 | Denzer et al. |
| 2015/0058960 A1 | 2/2015 | Schmoyer et al. |
| 2015/0066531 A1 | 3/2015 | Jacobson et al. |
| 2015/0081894 A1 | 3/2015 | Blomquist |
| 2015/0100038 A1 | 4/2015 | McCann et al. |
| 2015/0100787 A1 | 4/2015 | Westin et al. |
| 2015/0117234 A1 | 4/2015 | Raman et al. |
| 2015/0151051 A1 | 6/2015 | Tsoukalis |

(56) References Cited

U.S. PATENT DOCUMENTS

| | | |
|---|---|---|
| 2015/0161354 A1 | 6/2015 | Blomquist |
| 2015/0199192 A1 | 7/2015 | Borges et al. |
| 2015/0199485 A1 | 7/2015 | Borges et al. |
| 2015/0207626 A1 | 7/2015 | Neftel et al. |
| 2015/0220890 A1 | 8/2015 | Seshadri et al. |
| 2015/0230760 A1 | 8/2015 | Schneider |
| 2015/0281128 A1 | 10/2015 | Sindhu |
| 2015/0325064 A1 | 11/2015 | Downey |
| 2015/0328396 A1 | 11/2015 | Adams et al. |
| 2015/0352301 A1 | 12/2015 | Stedman et al. |
| 2015/0371004 A1 | 12/2015 | Jones |
| 2015/0379237 A1 | 12/2015 | Mills et al. |
| 2016/0001003 A1 | 1/2016 | Perazzo et al. |
| 2016/0006695 A1 | 1/2016 | Prodoehl et al. |
| 2016/0015885 A1 | 1/2016 | Pananen et al. |
| 2016/0034655 A1 | 2/2016 | Gray et al. |
| 2016/0045661 A1 | 2/2016 | Gray et al. |
| 2016/0063471 A1 | 3/2016 | Kobres et al. |
| 2016/0158437 A1 | 6/2016 | Biasi et al. |
| 2016/0228633 A1 | 8/2016 | Welsch et al. |
| 2016/0241391 A1 | 8/2016 | Fenster |
| 2016/0277152 A1 | 9/2016 | Xiang et al. |
| 2016/0285876 A1 | 9/2016 | Perez et al. |
| 2016/0317742 A1 | 11/2016 | Gannon et al. |
| 2016/0350513 A1 | 12/2016 | Jacobson et al. |
| 2016/0378618 A1 | 12/2016 | Cmielowski |
| 2017/0034277 A1 | 2/2017 | Jackson et al. |
| 2017/0063559 A1 | 3/2017 | Wallrabenstein |
| 2017/0099148 A1 | 4/2017 | Ochmanski et al. |
| 2017/0104645 A1 | 4/2017 | Wooton et al. |
| 2017/0111301 A1 | 4/2017 | Robinson |
| 2017/0140134 A1 | 5/2017 | Brough et al. |
| 2017/0146381 A1 | 5/2017 | Eckel et al. |
| 2017/0147761 A1 | 5/2017 | Moskal et al. |
| 2017/0149567 A1 | 5/2017 | Moskal |
| 2017/0149929 A1 | 5/2017 | Moskal |
| 2017/0214762 A1 | 7/2017 | Swain et al. |
| 2017/0258401 A1* | 9/2017 | Volpe .................. A61B 5/14542 |
| 2017/0258986 A1 | 9/2017 | Tsoiukalis |
| 2017/0262590 A1 | 9/2017 | Karakosta et al. |
| 2017/0274140 A1 | 9/2017 | Howard et al. |
| 2017/0286637 A1 | 10/2017 | Arrizza et al. |
| 2017/0325091 A1 | 11/2017 | Freeman et al. |
| 2017/0331804 A1 | 11/2017 | Jellison et al. |
| 2017/0351841 A1 | 12/2017 | Moskal |
| 2018/0063724 A1 | 3/2018 | Zhang et al. |
| 2018/0121613 A1 | 5/2018 | Connely, IV et al. |
| 2018/0122502 A1 | 5/2018 | Jones et al. |
| 2018/0126067 A1 | 5/2018 | Ledford et al. |
| 2018/0157821 A1 | 6/2018 | Fan |
| 2018/0181712 A1 | 6/2018 | Ensey et al. |
| 2018/0247712 A1 | 8/2018 | Muhsin et al. |
| 2018/0272117 A1 | 9/2018 | Fangrow |
| 2018/0278594 A1 | 9/2018 | Schiffman et al. |
| 2018/0317826 A1 | 11/2018 | Muhsin et al. |
| 2018/0322948 A1 | 11/2018 | Drost et al. |
| 2018/0359085 A1 | 12/2018 | Dervyn |
| 2019/0006044 A1 | 1/2019 | Brask |
| 2019/0030329 A1 | 1/2019 | Hannaman et al. |
| 2019/0036688 A1 | 1/2019 | Wasily et al. |
| 2019/0096518 A1 | 3/2019 | Pace |
| 2019/0132196 A1 | 5/2019 | Trivedi et al. |
| 2019/0166501 A1 | 5/2019 | Debates et al. |
| 2019/0172590 A1 | 6/2019 | Vesto et al. |
| 2019/0207965 A1 | 7/2019 | Espinosa |
| 2019/0228863 A1 | 7/2019 | Dharwad et al. |
| 2019/0229982 A1 | 7/2019 | Ikuta et al. |
| 2019/0243829 A1 | 8/2019 | Butler et al. |
| 2019/0244689 A1 | 8/2019 | Atkin |
| 2019/0245942 A1 | 8/2019 | Moskal |
| 2019/0311803 A1 | 10/2019 | Kohlbrecher et al. |
| 2019/0348160 A1 | 11/2019 | Heavelyn et al. |
| 2019/0392929 A1 | 12/2019 | Gassman |
| 2020/0023127 A1 | 1/2020 | Simpson et al. |
| 2020/0027541 A1 | 1/2020 | Xavier et al. |
| 2020/0027548 A1 | 1/2020 | Xavier et al. |
| 2020/0027549 A1 | 1/2020 | Xavier et al. |
| 2020/0027550 A1 | 1/2020 | Xavier et al. |
| 2020/0027551 A1 | 1/2020 | Xavier et al. |
| 2020/0028837 A1 | 1/2020 | Xavier et al. |
| 2020/0035355 A1 | 1/2020 | Xavier et al. |
| 2020/0054825 A1 | 2/2020 | Kamen et al. |
| 2020/0118692 A1* | 4/2020 | Booker .................. G06F 16/24 |
| 2020/0153627 A1 | 5/2020 | Wentz |
| 2020/0206413 A1 | 7/2020 | Silkaitis et al. |
| 2020/0220865 A1 | 7/2020 | Finger et al. |
| 2020/0282139 A1 | 9/2020 | Susi |
| 2020/0306443 A1 | 10/2020 | Day |
| 2020/0334497 A1 | 10/2020 | Barrett et al. |
| 2020/0335194 A1 | 10/2020 | Jacobson et al. |
| 2020/0351376 A1 | 11/2020 | Moskal |
| 2020/0353167 A1 | 11/2020 | Vivek et al. |
| 2020/0353168 A1 | 11/2020 | Keenan et al. |
| 2021/0014259 A1 | 1/2021 | Harris et al. |
| 2021/0020307 A1* | 1/2021 | Bhimavarapu .... G06Q 10/1097 |
| 2021/0043296 A1 | 2/2021 | Xavier et al. |
| 2021/0045640 A1 | 2/2021 | Poltorak |
| 2021/0050097 A1 | 2/2021 | Xavier et al. |
| 2021/0085855 A1 | 3/2021 | Belkin et al. |
| 2021/0098106 A1 | 4/2021 | Kohlbrecher et al. |
| 2021/0098107 A1 | 4/2021 | Xavier et al. |
| 2021/0105206 A1 | 4/2021 | Jha et al. |
| 2021/0252210 A1 | 8/2021 | Day et al. |
| 2021/0375438 A1 | 12/2021 | Xavier et al. |
| 2021/0409362 A1 | 12/2021 | Katis et al. |
| 2022/0037012 A1 | 2/2022 | Fryman |
| 2022/0062541 A1 | 3/2022 | Kamen et al. |
| 2022/0129452 A1 | 4/2022 | Butler et al. |
| 2022/0150307 A1 | 5/2022 | Walsh et al. |
| 2022/0165404 A1 | 5/2022 | Vivek et al. |
| 2022/0189605 A1 | 6/2022 | Kelly et al. |
| 2022/0223283 A1 | 7/2022 | Biasi et al. |
| 2022/0331513 A1 | 10/2022 | Howard et al. |
| 2022/0384059 A1 | 12/2022 | Xavier et al. |
| 2023/0009417 A1 | 1/2023 | Xavier et al. |
| 2023/0139360 A1 | 5/2023 | Kohlbrecher et al. |
| 2023/0145267 A1 | 5/2023 | Xavier et al. |
| 2023/0147762 A1 | 5/2023 | Xavier et al. |
| 2023/0253108 A1 | 8/2023 | Dharwad et al. |
| 2023/0298768 A1 | 9/2023 | Jacobson et al. |
| 2023/0320935 A1 | 10/2023 | Tagliamento |
| 2023/0410989 A1 | 12/2023 | Xavier et al. |
| 2024/0038358 A1 | 2/2024 | Xavier et al. |
| 2024/0047035 A1 | 2/2024 | Ruchti et al. |
| 2024/0071609 A1 | 2/2024 | Rohlwing |

FOREIGN PATENT DOCUMENTS

| | | |
|---|---|---|
| CA | 2 060 151 | 8/1997 |
| CA | 2 125 300 | 10/1999 |
| CA | 2 630 102 | 10/2008 |
| CA | 2 687 587 | 12/2008 |
| CA | 2 897 897 | 7/2014 |
| CA | 2 898 825 | 7/2014 |
| CA | 2 900 564 | 10/2014 |
| CA | 2 606 968 | 1/2020 |
| CN | 1759398 | 4/2006 |
| CN | 102521474 | 6/2012 |
| CN | 103816582 | 5/2014 |
| CN | 103920206 | 7/2014 |
| CN | 102300501 | 4/2015 |
| CN | 104487976 | 4/2015 |
| CN | 107810536 | 1/2023 |
| DE | 31 12 762 | 1/1983 |
| DE | 34 35 647 | 7/1985 |
| DE | 198 44 252 | 3/2000 |
| DE | 199 32 147 | 1/2001 |
| DE | 103 52 456 | 7/2005 |
| EP | 0 319 267 | 6/1989 |
| EP | 0 380 061 | 8/1990 |
| EP | 0 384 155 | 8/1990 |
| EP | 0 460 533 | 12/1991 |
| EP | 0 564 127 | 6/1993 |
| EP | 0 633 035 | 1/1995 |

(56)                    References Cited

FOREIGN PATENT DOCUMENTS

| EP | 0 652 528 | 5/1995 |
| EP | 0 672 427 | 9/1995 |
| EP | 0 683 465 | 11/1995 |
| EP | 0 880 936 | 12/1998 |
| EP | 1 050 993 | 11/2000 |
| EP | 1 157 711 | 11/2001 |
| EP | 1 174 817 | 1/2002 |
| EP | 0 664 102 | 4/2002 |
| EP | 1 197 178 | 4/2002 |
| EP | 0 830 775 | 8/2002 |
| EP | 1 500 025 | 4/2003 |
| EP | 1 487 171 | 7/2007 |
| EP | 1 933 497 | 6/2008 |
| EP | 2 026 223 | 2/2009 |
| EP | 2 113 842 | 11/2009 |
| EP | 2 228 004 | 9/2010 |
| EP | 2 243 506 | 10/2010 |
| EP | 2 410 448 | 1/2012 |
| EP | 2 742 961 | 6/2014 |
| EP | 2 874 087 | 5/2015 |
| ES | 2 371 995 | 1/2012 |
| FR | 2 717 919 | 9/1995 |
| GB | 2 285 135 | 6/1995 |
| JP | 04-161139 | 6/1992 |
| JP | 07-502678 | 3/1995 |
| JP | 11-500643 | 1/1999 |
| JP | 2000-316820 | 11/2000 |
| JP | 2002-531154 | 9/2002 |
| JP | 2003-016183 | 1/2003 |
| JP | 2003-296173 | 10/2003 |
| JP | 2003-308586 | 10/2003 |
| JP | 2005-021463 | 1/2005 |
| JP | 2005-527284 | 9/2005 |
| JP | 2005-284846 | 10/2005 |
| JP | 2006-047319 | 2/2006 |
| JP | 2006-520949 | 9/2006 |
| JP | 2007-518479 | 7/2007 |
| JP | 2007-525256 | 9/2007 |
| JP | 2008-080036 | 4/2008 |
| JP | 2008-516303 | 5/2008 |
| JP | 2008-158622 | 7/2008 |
| JP | 2008-529675 | 8/2008 |
| JP | 2009-163534 | 7/2009 |
| JP | 2010-502361 | 1/2010 |
| JP | 2011-506048 | 3/2011 |
| JP | 2012-011204 | 1/2012 |
| JP | 2012-070991 | 4/2012 |
| JP | 2012-523895 | 10/2012 |
| JP | 2014-068283 | 4/2014 |
| JP | 5647644 | 1/2015 |
| TW | 200426656 | 12/2004 |
| TW | I631966 | 8/2018 |
| WO | WO 84/001719 | 5/1984 |
| WO | WO 91/016416 | 10/1991 |
| WO | WO 92/010985 | 7/1992 |
| WO | WO 92/013322 | 8/1992 |
| WO | WO 94/005355 | 3/1994 |
| WO | WO 96/008755 | 3/1996 |
| WO | WO 96/025186 | 8/1996 |
| WO | WO 96/025963 | 8/1996 |
| WO | WO 98/012670 | 3/1998 |
| WO | WO 98/019263 | 5/1998 |
| WO | WO 99/051003 | 10/1999 |
| WO | WO 00/013580 | 3/2000 |
| WO | WO 00/053243 | 9/2000 |
| WO | WO 01/014974 | 3/2001 |
| WO | WO 01/033484 | 5/2001 |
| WO | WO 01/045014 | 6/2001 |
| WO | WO 01/083007 | 11/2001 |
| WO | WO 02/005702 | 1/2002 |
| WO | WO 02/036044 | 5/2002 |
| WO | WO 02/049153 | 6/2002 |
| WO | WO 02/049279 | 6/2002 |
| WO | WO 02/069099 | 9/2002 |
| WO | WO 02/081015 | 10/2002 |
| WO | WO 02/088875 | 11/2002 |
| WO | WO 03/006091 | 1/2003 |
| WO | WO 03/023551 | 3/2003 |
| WO | WO 03/050917 | 6/2003 |
| WO | WO 03/091836 | 11/2003 |
| WO | WO 03/094092 | 11/2003 |
| WO | WO 2004/060455 | 7/2004 |
| WO | WO 2004/070557 | 8/2004 |
| WO | WO 2004/070562 | 8/2004 |
| WO | WO 2004/072828 | 8/2004 |
| WO | WO 2005/036447 | 4/2005 |
| WO | WO 2005/057175 | 6/2005 |
| WO | WO 2005/066872 | 7/2005 |
| WO | WO 2007/087443 | 8/2007 |
| WO | WO 2007/117705 | 10/2007 |
| WO | WO 2007/127879 | 11/2007 |
| WO | WO 2007/127880 | 11/2007 |
| WO | WO 2008/059495 | 5/2008 |
| WO | WO 2008/064254 | 5/2008 |
| WO | WO 2008/067245 | 6/2008 |
| WO | WO 2008/082854 | 7/2008 |
| WO | WO 2008/088490 | 7/2008 |
| WO | WO 2008/097316 | 8/2008 |
| WO | WO 2008/103915 | 8/2008 |
| WO | WO 2008/124478 | 10/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/036327 | 3/2009 |
| WO | WO 2009/049252 | 4/2009 |
| WO | WO 2010/017279 | 2/2010 |
| WO | WO 2010/033919 | 3/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/130992 | 11/2010 |
| WO | WO 2010/135646 | 11/2010 |
| WO | WO 2010/135654 | 11/2010 |
| WO | WO 2010/135686 | 11/2010 |
| WO | WO 2011/005633 | 1/2011 |
| WO | WO 2011/022549 | 2/2011 |
| WO | WO 2012/048833 | 4/2012 |
| WO | WO 2012/049214 | 4/2012 |
| WO | WO 2012/049218 | 4/2012 |
| WO | WO 2012/120078 | 9/2012 |
| WO | WO 2012/140547 | 10/2012 |
| WO | WO 2012/164556 | 12/2012 |
| WO | WO 2012/170942 | 12/2012 |
| WO | WO 2013/045506 | 4/2013 |
| WO | WO 2014/100736 | 6/2014 |
| WO | WO 2014/131729 | 9/2014 |
| WO | WO 2014/131730 | 9/2014 |
| WO | WO 2015/047595 | 4/2015 |
| WO | WO 2015/124569 | 8/2015 |
| WO | WO 2016/179389 | 11/2016 |
| WO | WO 2017/200989 | 11/2017 |
| WO | WO 2019/219290 | 11/2019 |
| WO | WO 00/003344 | 1/2020 |
| WO | WO 2020/227403 | 11/2020 |
| WO | WO 2021/201884 | 10/2021 |
| WO | WO 2022/006014 | 1/2022 |
| WO | WO 2022/051230 | 3/2022 |
| WO | WO 2023/159134 | 8/2023 |

OTHER PUBLICATIONS

Akridge, Jeannie, "New Pumps Outsmart User Error", Healthcare Purchasing News, Apr. 2011, pp. 10, <http://web.archive.org/web/20110426122450/http://www.hpnonline.com/inside/2011-04/1104-OR-Pumps.html>.

Alur et al., "Formal Specifications and Analysis of the Computer-Assisted Resuscitation Algorithm (CARA) Infusion Pump Control

(56) References Cited

OTHER PUBLICATIONS

System", International Journal on Software Tools for Technology Transfer, Feb. 2004, vol. 5, No. 4, pp. 308-319.

Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.

ASHP Advantage, "Improving Medication Safety in Health Systems Through Innovations in Automation Technology", Proceedings of Educational Symposium and Educational Sessions during the 39th ASHP Midyear Clinical Meeting, Dec. 5-9, 2004, Orlando, FL, pp. 28.

Beard et al., "Total Quality Pain Management: History, Background, Resources", Abbott Laboratories, TQPM Survey History, available Feb. 2015 or earlier, pp. 1-3.

Bektas et al., "Bluetooth Communication Employing Antenna Diversity", Proceedings of Eight IEEE International Symposium on Computers and Communication, Jul. 2003, pp. 6.

Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.

Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.

Braun, "Infusomat® Space and Accessories", Instructions for Use, Nov. 2010, pp. 68. <http://corp.bbraun.ee/Extranet/Infusionipumbad/Kasutusjuhendid/Vanad/Kasutusjuhend-Infusomat_Space(vers688J,inglise_k).pdf>.

Brownlee, Seth, "Product Spotlight: The Plum A+ with Hospira MedNet Infusion System", PP&P Magazine, Dec. 2005, vol. 2, No. 7, pp. 2.

Cannon, MD et al., "Automated Heparin-Delivery System to Control Activated Partial Thromboplastin Time", Circulation, Feb. 16, 1999, vol. 99, pp. 751-756.

Cardinal Health, "Alaris® Syringe Pumps" Technical Service Manual, Copyright 2002-2006, Issue 9, pp. 1-88, <http://www.frankshospitalworkshop.com/equipment/documents/infusion_pumps/service_manuals/Cardinal_Alaris_-_Service_Manual.pdf>.

"CareAware@ Infusion Management", Cerner Store, as printed May 12, 2011, pp. 3, <https://store.cerner.com/items/7>.

Chen et al., "Enabling Location-Based Services on Wireless LANs", The 11th IEEE International Conference on Networks, ICON 2003, Sep. 28-Oct. 1, 2003, pp. 567-572.

"Computer Dictionary", Microsoft Press, Third Edition, Microsoft Press, 1997, pp. 430 & 506.

"Context-Free Grammar", Wikipedia.org, as last modified Mar. 5, 2010 in 11 pages, <https://en.wikipedia.org/w/index.php/?title=Context-free_grammar&oldid=347915989>.

Crawford, Anne J., MSN, RNC, "Building a Successful Quality Pain Service: Using Patient Satisfaction Data and the Clinical Practice Guideline", USA, 1995, pp. 1-6.

Crocker et al., "Augmented BNF for Syntax Specifications: ABNF", Network Working Group, Standards Track, Jan. 2008, pp. 16.

Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.

Davies, T., "Cordless Data Acquisition in a Hospital Environment", IEE Colloquium on Cordless Computing—Systems and User Experience, 1993, pp. 4.

Dayhoff et al., "Medical Data Capture and Display: The Importance of Clinicians' Workstation Design", AMIA, Inc., 1994, pp. 541-545.

Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.

"Download", Free On-Line Dictionary of Computing, as archived Jun. 16, 2010 in 1 page, http://web.archive.org/web/20100616010314/https://foldoc.org/download.

East PhD et al., "Digital Electronic Communication Between ICU Ventilators and Computers and Printers", Respiratory Care, Sep. 1992, vol. 37, No. 9, pp. 1113-1122.

Edworthy, Judy, "Medical Audible Alarms: A Review", Journal of the American Medical Informatics Association, vol. 20, No. 3, 2013, pp. 584-589.

Einhorn, George W., "Total Quality Pain Management: A Computerized Quality Assessment Tool for Postoperative Pain Management", Abbott Laboratories, Chicago, IL, Mar. 2, 2000, pp. 1-4.

Eskew et al., "Using Innovative Technologies to Set New Safety Standards for the Infusion of Intravenous Medications", Hospital Pharmacy, 2002, vol. 37, No. 11, pp. 1179-1189.

Felleiter et al., "Data Processing in Prehospital Emergency Medicine", International journal of Clinical Monitoring and Computing, Feb. 1995, vol. 12, No. 1, pp. 37-41.

"File Verification", Wikipedia.org, as last modified Oct. 11, 2011 in 2 pages, <https://en.wikipedia.org/w/index.php?title=File_verification&oldid=455048290>.

Fogt et al., Development and Evaluation of a Glucose Analyzer for a Glucose-Controlled Insulin Infusion System (Biostator®), Clinical Chemistry, 1978, vol. 24, No. 8, pp. 1366-1372.

Gabel et al., "Camp: A Common API for Measuring Performance", 21st Large Installations System Administration Conference (LISA '07), 2007, pp. 49-61.

Gage et al., "Automated Anesthesia Surgery Medical Record System", International Journal of Clinical Monitoring and Computing, Dec. 1990, vol. 7, No. 4, pp. 259-263.

Galt et al., "Personal Digital Assistant-Based Drug Information Sources: Potential to Improve Medication Safety", Journal of Medical Library Association, Apr. 2005, vol. 93, No. 2, pp. 229-236.

Gardner, Ph.D. et al., "Real Time Data Acquisition: Recommendations for the Medical Information Bus (MIB)", 1992, pp. 813-817.

"General-Purpose Infusion Pumps", Health Devices, EXRI Institute, Oct. 1, 2002, vol. 31, No. 10, pp. 353-387.

Givens et al., "Exploring the Internal State of User Interfaces by Combining Computer Vision Techniques with Grammatical Inference", Proceedings of the 2013 International Conference on Software Engineering, San Francisco, CA, May 18-26, 2013, pp. 1165-1168.

Glaeser, "A Hierarchical Minicomputer System for Continuous Post-Surgical Monitoring", Computers and Biomedical Research, Aug. 31, 1975, pp. 336-361.

Goldberg et al., "Clinical Results of an Updated Insulin Infusion Protocol in Critically Ill Patients", Diabetes Spectrum, 2005, vol. 18, No. 3, pp. 188-191.

Gomez et al., "CLAM: Connection-Less, Lightweight, and Multiway Communication Support for Distributed Computing", Computer Science, 1997, vol. 1199, pp. 227-240.

"GPS Tracker for Medical Equipment", <http://www.trackingsystem.com/forbusinesses/corporate-trackingsystem/1098-gps-tracker-formedicalequipment.html>, Mar. 15, 2015, pp. 2.

Graseby, "Model 3000/500 and Micro 3100/505: Volumetric Infusion Pump", Technical Service Manual, Graseby Medical Ltd., Apr. 2002, Issue A, pp. 160.

Graseby, "Model 3000/500 and Micro 3100/505: Volumetric Infusion Pump: Illustrated Parts List for Pump Serial Numbers from 3000 to 59,999", Technical Service Manual, Graseby Medical Ltd., Apr. 2002, Issue A, pp. 71.

Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.

Hamann et al., "PUMPSIM: A Software Package for Simulating Computer-Controlled Drug Infusion Pumps", Annual International Conference of the IEEE Engineering in Medicine and Biology Society, 1990, vol. 12, No. 5, pp. 2019-2020.

Hasegawa et al., "On a Portable Memory Device for Physical Activities and Informations of Maternal Perception", Journal of Perinatal Medicine, 1988, vol. 16, No. 4, pp. 349-356.

Hawley et al., "Clinical Implementation of an Automated Medical Information Bus in an Intensive Care Unit", Proceedings of the Annual Symposium on Computer Application in Medical Care, Nov. 9, 1988, pp. 621-624.

(56) References Cited

OTHER PUBLICATIONS

Hayes-Roth et al., "Guardian: A Prototype Intelligent Agent for Intensive-Care Monitoring", Artificial Intelligence in Medicine, vol. 4, Dec. 31, 1992, pp. 165-185.
Hospira, GemStar® Pain Management Infusion System 9-084-PR1-2-2, <www.hospira.com/products/gemstar_painmanagement.aspx>, Jan. 28, 2010, pp. 1-2.
Introducing Abbott TQPM (Total Quality Pain Management), Abbott Laboratories, Abbott Park, IL, May 2000, pp. 1-4.
"Infusion Pump", Wikipedia.org, as last modified Mar. 27, 2014, in 3 pages, <https://web.archive.org/web/20140703024932/https://en.wikipedia.org/wiki/Infusion_pump>.
Isaka et al., "Control Strategies for Arterial Blood Pressure Regulation", IEEE Transactions on Biomedical Engineering, Apr. 1993, vol. 40, No. 4, pp. 353-363.
Johnson et al., "Using BCMA Software to Improve Patient Safety In Veterans Administration Medical Centers", Journal of Healthcare Information Management, Dec. 6, 2004, vol. 16, No. 1, pp. 46-51.
Kent Displays, "Reflex™ Electronic Skins", Product Brief 25127B, 2009, pp. 2.
Kent Displays, "Reflex Electronic Skins Engineering Evaluation Kit", 25136A, Mar. 10, 2009.
Lefkowitz et al., "A Trial of the Use of Bar Code Technology to Restructure a Drug Distribution and Administration System", Hospital Pharmacy, Mar. 31, 1991, vol. 26, No. 3, pp. 239-242.
Lenssen et al., "Bright Color Electronic Paper Technology and Applications", IDS '09 Publication EP1-2 (Phillips Research), 2009, pp. 529-532.
Leveson, Nancy, "Medical Devices: The Therac-25", Appendix A, University of Washington, 1995, pp. 49.
Linkens, D.A. "Computer Control for Patient Care", Computer Control of Real-Time Processes, IEE Control Engineering Series 41, 1990, Ch. 13, pp. 216-238.
Mako Hill et al., "The Official Ubuntu Book", Shoeisha Co., Ltd., 1st Edition, Jun. 11, 2007, pp. 115 to 125.
Marshall, et al., "New Microprocessor-Based Insulin Controller", IEEE Transactions on Biomedical Engineering, Nov. 1983, vol. BME-30, No. 11, pp. 689-695.
Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.
Matsunaga et al., "On the Use of Machine Learning to Predict the Time and Resources Consumed by Applications", 2010 10th IEEE/ACM International Conference on Cluster, Cloud and Grid Computing (CCGrid), May 17-20, 2010, pp. 495-504.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
"McKesson Automation and ALARIS Medical Systems Developing Point-of-Care Bar Coding Solution to Improve IV Medication Safety", PR Newswire, NY, Dec. 9, 2002, pp. 4.
Medfusion™, "Medfusion Syringe Infusion Pump Model 4000", Operator's Manual, Software Version V1.1, Sep. 2011, pp. 154. <http://www.medfusionpump.com/assets/literature/manuals/Operators_Manual_4000_40-5760-51A.pdf>.
Metnitz et al., "Computer Assisted Data Analysis in Intensive Care: the ICDEV Project-Development of a Scientific Database System for Intensive Care", International Journal of Clinical Monitoring and Computing, Aug. 1995, vol. 12, No. 3, pp. 147-159.
Micrel Medical Devices, "MP Daily +" <http://web.archive.org/web/20130803235715/http://www.micrelmed.com/index.aspx?productid=9> as archived Aug. 3, 2013 in 1 page.
Moghissi, Etie, MD, FACP, FACE, "Hyperglycemia in Hospitalized Patients", A Supplement to ACP Hospitalist, Jun. 15, 2008, pp. 32.
Murray, Jr. et al., "Automated Drug Identification System (during surgery)", IEEE Proceedings of Southeastcon '91, Apr. 7-10, 1991, pp. 265.

Nicholson et al., "'Smart' Infusion Apparatus for Computation and Automated Delivery of Loading, Tapering, and Maintenance Infusion Regimens of Lidocaine, Procainamide, and Theophylline", Proceedings of The Seventh Annual Symposium on Computer Applications in Medical Care, Oct. 1983, pp. 212-213.
Nolan et al., "The P1073 Medical Information Bus Standard: Overview and Benefits for Clinical Users", 1990, pp. 216-219.
Omnilink Systems, Inc., "Portable Medical Equipment Tracking", <http://www.omnilink.com/portablemedicalequipmenttracking/>, Mar. 15, 2015, pp. 2.
O'Shea, Kristen L., "Infusion Management: Working Smarter, Not Harder", Hospital Pharmacy, Apr. 2013, vol. 48, No. 3, pp. S1-S14.
Package Management in Debian GNU/Linux, Debian GNU/Linux Expert Desktop Use Special, Giutsu-Hyohron Co., Ltd., First Edition, Sep. 25, 2004, pp. 183-185.
Passos et al., "Distributed Software Platform for Automation and Control of General Anaesthesia", Eighth International Symposium on Parallel and Distributed Computing, ISPDC '09, Jun. 30-Jul. 4, 2009, pp. 8.
Philips, "IntelliSpace Event Management and IntelliVue Patient Monitoring", Release 10, 2011, <http://incenter.medical.philips.com/doclib/enc/fetch/2000/4504/577242/577243/577247/582646/583147/8359175/Philips_Patient_Monitoring_and_IntelliSpace_Event_Management_Interoperability.pdf%3fnodeid%3d8508574%26vernum%3d-2>, pp. 2.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Rappoport, Arthur E., "A Hospital Patient and Laboratory machine-Readable Identification System (MRIS) Revisited", Journal of Medical Systems, Apr. 1984, vol. 8, Nos. 1/2, pp. 133-156.
Ritchie et al., "A Microcomputer Based Controller for Neuromuscular Block During Surgery", Annals of Biomedical Engineering, Jan. 1985, vol. 13, No. 1, pp. 3-15.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sanders et al., "The Computer in a Programmable Implantable Medication System (PIMS)", Proceedings of the Annual Symposium on Computer Application in Medical Care, Nov. 2, 1982, pp. 682-685.
Schilling et al., "Optimizing Outcomes! Error Prevention and Evidence-Based Practice with IV Medications", A Pro-Ce Publication, Hospira, Inc., Feb. 6, 2012, pp. 56.
Schulze et al., "Advanced Sensors Technology Survey", Final Report, Feb. 10, 1992, pp. 161.
Scott, et al., "Using Bar-Code Technology to Capture Clinical Intervention Data in a Hospital with a Stand-Alone Pharmacy Computer System", Mar. 15, 1996, American Journal of Health-System Pharmacy, vol. 53, No. 6, pp. 651-654.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.
Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.
Sheppard, Louis, Ph.D., "Computer Control of the Infusion of Vasoactive Drugs", Annals of Biomedical Engineering, Jul. 1980, vol. 8, No. 4-6, pp. 431-444.
Sheppard, Louis, Ph.D., "The Application of Computers to the Measurement, Analysis, and Treatment of Patients Following Cardiac Surgical Procedures", The University of Alabama in Birmingham, Oct. 31, 1977, pp. 297-300.
Sheppard, Louis, Ph.D., "The Computer in the Care of Critically Ill Patients", Proceedings of the IEEE, Sep. 1979, vol. 67, No. 9, pp. 1300-1306.

(56)      References Cited

OTHER PUBLICATIONS

"Sigma Spectrum: Operator's Manual", Oct. 2009, pp. 72. <http://static.medonecapital.com/manuals/userManuals/Sigma-Spectrum-Operator-Manual-October-2009.pdf>.

Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.

Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. <http://www.thomasland.com/hpj4209-832.pdf>.

Slack, W.V., "Information Technologies for Transforming Health Care", <https://www.andrew.cmu.edu/course/90-853/medis.dir/otadocs.dir/03ch2.pdf>, Ch. 2, 1995, pp. 29-78.

Smith, Joe, "Infusion Pump Informatics", CatalyzeCare: Transforming Healthcare, as printed May 12, 2011, pp. 2.

Sodders, Lisa, "VA Center Keeps Medicine in Right Hands", The Capital-Journal, Dec. 4, 1999, pp. 1-2.

"Software Versioning", Wikipedia.org, dated Oct. 16, 2011 in 11 pages, <https://en.wikipedia.org/w/index.php?title=Software_versioning&oldid=455859110>.

Stitt, F.W., "The Problem-Oriented Medical Synopsis: a Patient-Centered Clinical Information System", Proceedings of the Annual Symposium on Computer Application in Medical Care, 1994, pp. 88-92.

Stokowski, Laura A. RN, MS, "Using Technology to Improve Medication Safety in the Newborn Intensive Care Unit", Advances in Neonatal Care, Dec. 2001, vol. 1, No. 2, pp. 70-83.

Sutton et al., "The Syntax and Semantics of the PROforma Guideline Modeling Language", Journal of the American Medical Informatics Association, Sep./Oct. 2003, vol. 10, No. 5, pp. 433-443.

Szeinbach et al., "Automated Dispensing Technologies: Effect on Managed Care", Journal of Managed Care Pharmacy (JMCP), Sep./Oct. 1995, vol. 1, No. 2, pp. 121-127.

Szolovits et al., "Guardian Angel: Patient-Centered Health Information Systems", Technical Report MIT/LCS/TR-604, Massachusetts Institute of Technology Laboratory for Computer Science, May 1994, pp. 39.

Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.

Van Den Berghe, M.D., Ph.D., et al., "Intensive Insulin Therapy in the Medical ICU", The New England Journal of Medicine, Feb. 2, 2006, vol. 354, No. 5, pp. 449-461.

Van Der Maas et al., "Requirements for Medical Modeling Languages", Journal of the American Medical Informatics Association, Mar./Apr. 2001, vol. 8, No. 2, pp. 146-162.

Villalobos et al., "Computerized System in Intensive Care medicine", Medical Informatics, vol. 11, No. 3, 1986, pp. 269-275.

Wilkins et al., "A Regular Language: The Annotated Case Report Form", PPD Inc., PharmaSUG2011—Paper CD18, 2011, pp. 1-9.

Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, Nov.-Dec. 1994, pp. 671-677.

Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.

Yurkonis et al., "Computer Simulation of Adaptive Drug Infusion", IEEE Transactions on Biomedical Engineering, vol. BME-34, No. 8, Aug. 1987, pp. 633-635.

Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.

Bellare et al., "Security Proofs for Identity-Based Identification and Signature Schemes", Lecture Notes in Computer Science, Jan. 2009, vol. 22, No. 1, pp. 18.

Block, Alexander, "Secret Sharing and 1-11 Threshold Signatures with BLS", Jul. 2, 2018, https://blog.dash.org/secret-sharing-and-threshold-signatures-with-bls-954d1587b5f, in 8 pages.

Doesburg et al., "Improved Usability of a Multi-Infusion Setup Using a Centralized Control Interface: A Task-Based Usability Test", Aug. 11, 2017, PLoS ONE, vol. 12, No. 8, pp. 10.

Gutwin et al., "Gone But Not Forgotten: Designing for Disconnection in Synchronous Groupware", CSCW 2010, Feb. 6-10, 2010, Savannah, Georgia, USA., pp. 179-188.

Huang et al., "Secure Identity-Based Data Sharing and Profile Matching for Mobile Healthcare Social Networks in Cloud Computing", vol. 6, Jul. 2018, pp. 36584-36594.

International Search Report and Written Opinion received in PCT Application No. PCT/US2021/039457, dated Oct. 13, 2021 in 7 pages.

International Preliminary Report on Patentability and Written Opinion received in PCT Application No. PCT/US2021/039457, dated Feb. 14, 2023 in 8 pages.

Li et al., "Hijacking an Insulin Pump: Security Attacks and Defenses for a Diabetes Therapy System", 2011 IEEE 13th International Conference on e-Health Networking, Applications and Services, 2011, pp. 150-156.

Michienzi, Kelly, "Managing Drug Library Updates", Pharmacy Purchasing Products, https://www.pppmag.com/article/1061, Feb. 2012, vol. 9, pp. 22-23.

Murphy, Robert, "The Design of Safety-Critical Medical Infusion Devices", May 30, 2007, Doctor of Philosophy submission, pp. 317.

Nojoumian et al., "Social Secret Sharing in Cloud Computing Using a New Trust Function", 2012 Tenth Annual International Conference on Privacy, Security and Trust, pp. 161-167.

Rahmani et al., "Smart e-Health Gateway: Bringing Intelligence to Internet-of-Things Based Ubiquitous Healthcare Systems", 2015 12th Annual IEEE Consumer Communications and Networking Conference (CCNC), Jul. 2015, pp. 826-834.

Sethia et al., "Security Framework for Portable NFC Mobile Based Health Record System", Oct. 2016, IEEE 12th International Conference on Wireless and Mobile Computing, Networking and Communications, pp. 1-8.

"Sigma Spectrum: Operator's Manual", May 15, 2008, pp. 63. <https://usme.com/content/manuals/sigma-spectrum-operator-manual.pdf>.

Solapurkar et al., "Building Secure Healthcare Services Using OAuth 2.0 and JSON Web Token in IOT Cloud Scenario", Dec. 2016, 2nd International Conference on Contemporary Computing and Informatics, pp. 99-10.

"TCG TPM v2.0 Provisioning Guidance", Reference, Version 1, Revision 1, Mar. 15, 2017, pp. 1-43.

Yoo et al., "Code-Based Authentication Scheme for Lightweight Integrity Checking of Smart Vehicles", IEEE Access, 2018, vol. 6, pp. 46731-46741.

* cited by examiner

600

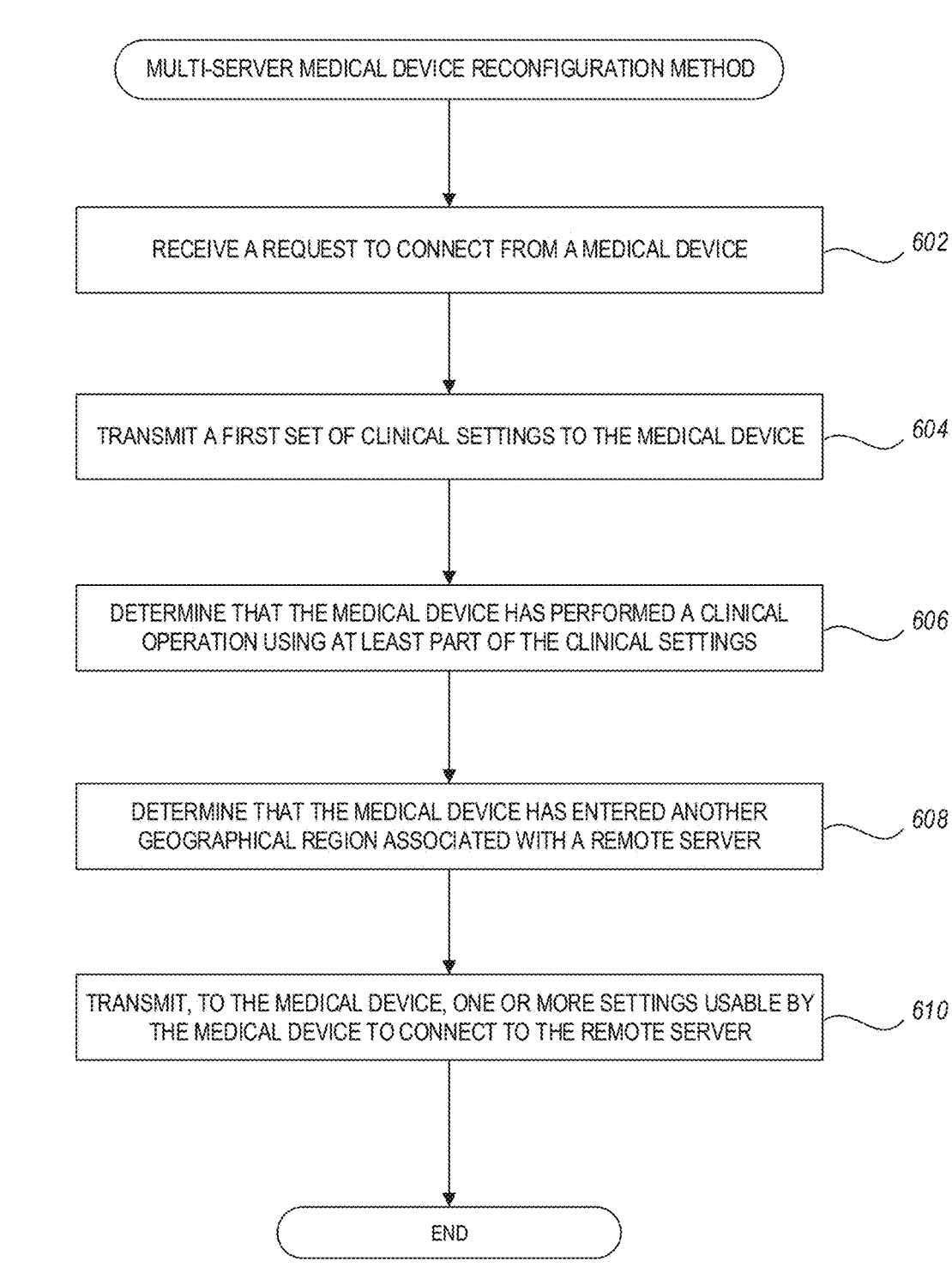

MULTI-SERVER MEDICAL DEVICE RECONFIGURATION METHOD

RECEIVE A REQUEST TO CONNECT FROM A MEDICAL DEVICE — 602

TRANSMIT A FIRST SET OF CLINICAL SETTINGS TO THE MEDICAL DEVICE — 604

DETERMINE THAT THE MEDICAL DEVICE HAS PERFORMED A CLINICAL OPERATION USING AT LEAST PART OF THE CLINICAL SETTINGS — 606

DETERMINE THAT THE MEDICAL DEVICE HAS ENTERED ANOTHER GEOGRAPHICAL REGION ASSOCIATED WITH A REMOTE SERVER — 608

TRANSMIT, TO THE MEDICAL DEVICE, ONE OR MORE SETTINGS USABLE BY THE MEDICAL DEVICE TO CONNECT TO THE REMOTE SERVER — 610

END

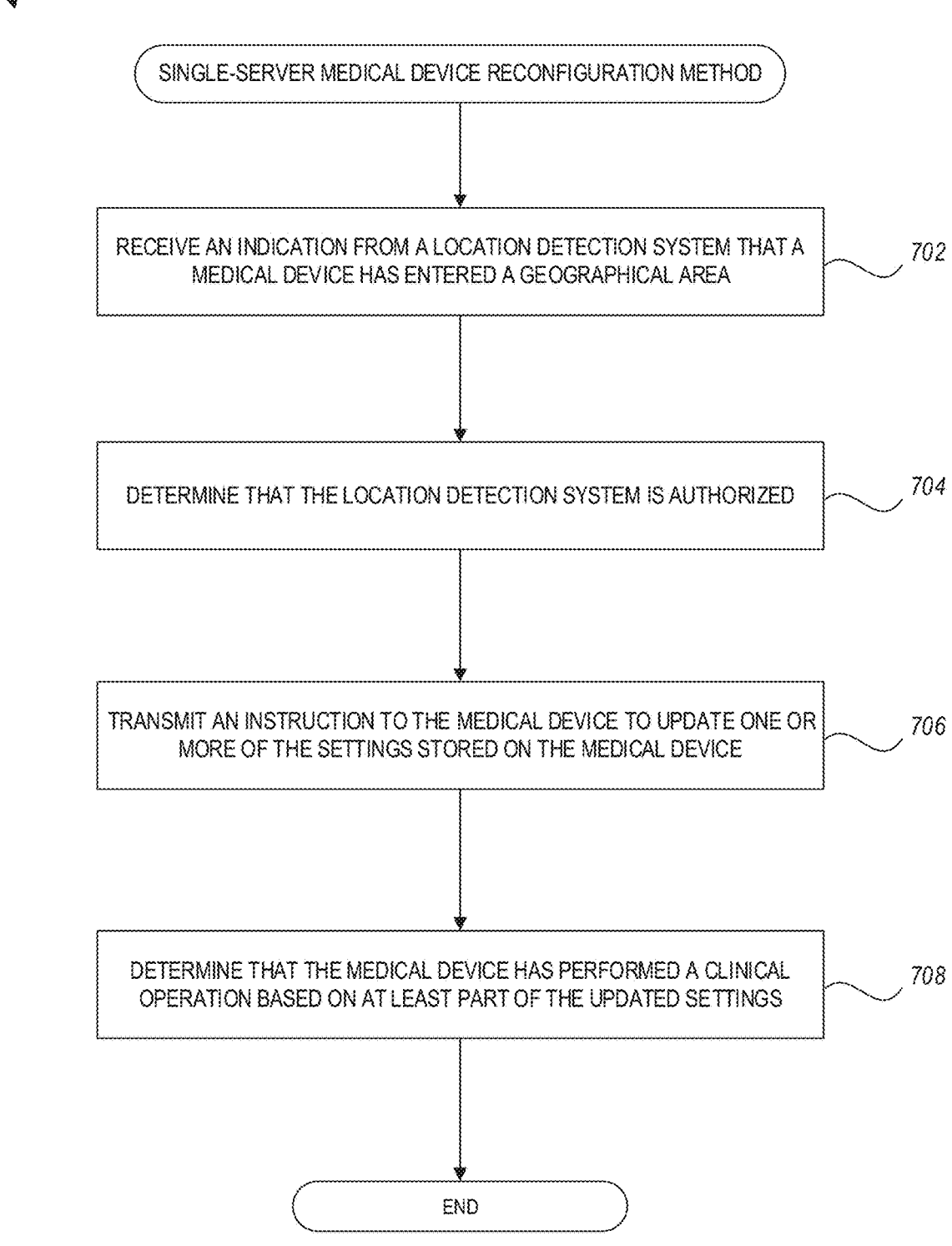

SINGLE-SERVER MEDICAL DEVICE RECONFIGURATION METHOD

RECEIVE AN INDICATION FROM A LOCATION DETECTION SYSTEM THAT A MEDICAL DEVICE HAS ENTERED A GEOGRAPHICAL AREA — 702

DETERMINE THAT THE LOCATION DETECTION SYSTEM IS AUTHORIZED — 704

TRANSMIT AN INSTRUCTION TO THE MEDICAL DEVICE TO UPDATE ONE OR MORE OF THE SETTINGS STORED ON THE MEDICAL DEVICE — 706

DETERMINE THAT THE MEDICAL DEVICE HAS PERFORMED A CLINICAL OPERATION BASED ON AT LEAST PART OF THE UPDATED SETTINGS — 708

END

*FIG. 7*

LOCATION-BASED RECONFIGURATION OF INFUSION PUMP SETTINGS

INCORPORATION BY REFERENCE TO ANY PRIORITY APPLICATIONS

This application claims priority to Indian Patent Application No. 202011028208, filed on Jul. 2, 2020 and titled "LOCATION-BASED RECONFIGURATION OF INFUSION PUMP SETTINGS," and U.S. Provisional Application No. 63/068,798, filed on Aug. 21, 2020 and titled "LOCATION-BASED RECONFIGURATION OF INFUSION PUMP SETTINGS," the disclosures of which are incorporated herein by reference in their entirety. Any and all applications for which a foreign or domestic priority claim is identified in the Application Data Sheet as filed with the present application are hereby incorporated herein by reference in their entirety under 37 CFR 1.57.

TECHNICAL FIELD

This disclosure relates to the field of medical devices, and particularly to techniques for reconfiguring a medical device based on detection of change in the location of the medical device.

BACKGROUND

Medical devices capable of performing various clinical operations are commonplace in modern hospital environments. Such medical devices may connect to a hospital network using predetermined network settings and communicate with other devices on the hospital network. Such medical devices may also store rules that govern the clinical operations available on the medical devices to improve patient safety.

SUMMARY

Various techniques for updating the settings on a medical device based on the location of the medical device are described herein. Although many of the examples are described in the context of a hospital environment, the techniques described herein can be applied to any environment in which medical devices can operate. The medical devices described herein may be infusion pumps, other medical devices, or any combinations thereof. The settings described herein may be network settings, infusion settings, drug library settings, other medical device settings, or any combinations thereof. For example, an infusion pump can be moved across different rooms and clinical care areas (CCAs) within a hospital, or even to different hospitals. As the location of the infusion pump changes, the settings on the infusion pump may need to be updated (e.g., for proper network connectivity, date update, and compliance with safety standards, and the like).

According to embodiments of the present disclosure, the settings of a medical device may be re-configured or otherwise changed upon detecting that the medical device has entered a designated area, exited a designated area, or both. These and other embodiments are described in greater detail below with reference to FIGS. 1-7.

BRIEF DESCRIPTION OF THE DRAWINGS

The embodiments described herein are illustrated by way of example, and not by way of limitation, in the figures of the accompanying drawings in which like references indicate similar elements.

FIG. 6 is a flow chart illustrating an example multi-server medical device reconfiguration method in accordance with aspects of this disclosure.

FIG. 7 is a flow chart illustrating an example single-server medical device reconfiguration method in accordance with aspects of this disclosure.

DETAILED DESCRIPTION

Introduction

A hospital environment may include medical devices, such as infusion pumps, that are mobile and moved to and from different areas of the hospital environment. The hospital environment may be a hospital having a central server that communicates with the medical devices within the hospital. Such medical devices may need to be connected to the central server via a wired or wireless connection to perform their clinical operations (e.g., an infusion pump may initiate infusion therapies on patients in response to instructions from the central server).

The hospital environment described herein may include a single hospital building, a multi-building hospital facility, or a multi-facility hospital network. The buildings and/or facilities may be close to each other or spread out over multiple cities, states, countries, etc., and may belong to a single entity or enterprise or belong to different entities or enterprises.

When a medical device is moved from one area to another, the settings stored on the medical device may need to be updated. For example, the network settings on the medical device may need to be updated so that the medical device can access the network in the new area (e.g., the Wi-Fi network) and communicate with the correct server in the new area to receive clinical commands (e.g., a command to start an infusion therapy). As another example, the safety settings on the medical device may need to be updated so that the medical device is in compliance with the safety protocols in the new area (especially if the new area has stricter safety standards), for example, to allow fewer drug types, stricter limits on volume infused, and the like. One method of updating the settings stored on the medical device is for a biomedical engineer to manually reconfigure the settings on the medical device when the medical device is first moved into the new area. However, such a method requires notifying the biomedical engineer of the change in the location of the medical device and ensuring that the biomedical engineer is available to update the settings on the medical device, which would consume a significant amount of human resources. Further, such a method may not be sufficiently responsive, especially in emergency situations.

Thus, an improved method of detecting a change in the location of a medical device and reconfiguring the settings on the medical device is desired.

Figure 1:
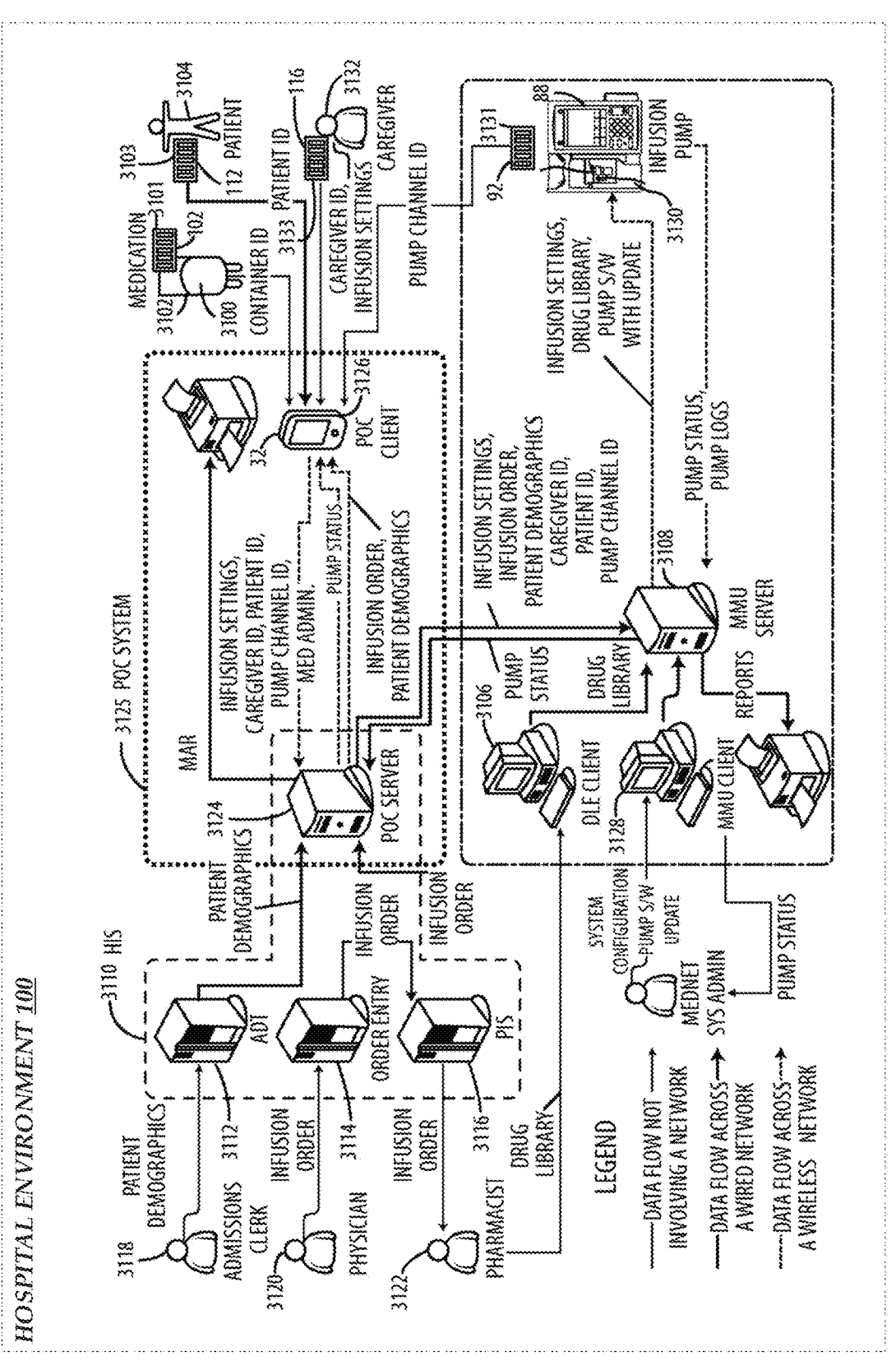
FIG. 1 is a schematic diagram of an example hospital environment including one or more medical devices in accordance with aspects of this disclosure.

With reference to FIG. 1, an example hospital environment in which one or more of the medical device reconfiguration techniques of the present disclosure may be utilized is described. Following the discussion of FIG. 1, specific details of the various embodiments of the present disclosure are described with reference to FIGS. 2-7.

Overview of Example Hospital Environment

FIG. 1 illustrates one embodiment of a system for administering medication via an infusion pump in a hospital environment 100. The medication management system (MMS) shown in FIG. 1 includes a medication management unit (MMU) server 3108 and a medical device, such as infusion pump 3130, operating in conjunction with one or more information systems or components of a hospital environment.

Intravenous (IV) fluid(s) and/or medication(s) 3100 in containers 3102 may be administered to a patient 3104 using the system shown in FIG. 1. Although the system shown in FIG. 1 utilizes barcodes and a barcode reader as apparatus to input and read machine-readable information, those skilled in the art will appreciate that other apparatus for reading or inputting information may be utilized. Moreover, a point of care (POC) client 3126 may include an identification receiver 32 adapted to recognize such indicia may be provided in the MMS.

In certain aspects, the IV fluids and/or medications 3100 in container 3102 may be provided with new or supplemental labels with a unique infusion order identifying barcode by a pharmacist according to certain hospital practices. Specifically, drug container specific identification information, such as barcoded information on the container 3102 may include patient identification information, medication identification information, universal identification information, medical device delivery information, and/or medication order information. The IV fluids and/or medications 3100 in barcode-identified containers 3102 may be supplied to hospitals by various vendors, with preexisting unique barcode identifiers, which include medication information and other information, such as a National Disease Center (NDC) code, expiration information, drug interaction information, and the like.

In some aspects of the disclosure, the universal identification information on the container 3102 may be a unique medication order identifier that, by itself, identifies the order associated with the container. In other aspects, the identification information on the container 3102 may be a composite patient/order code that contains both a patient ID (such as a medical record number) and an order ID unique only within the context of the patient. In certain aspects, the identification information on the container 3102 may include a medication ID. The system identified in FIG. 1 may include a drug library editor (DLE) client 3106, such as a notebook, desktop or server computer. The DLE client 3106 may include DLE software. As described above, the MMU server 3108 may have MMU software that is installed and runs on the MMU server 3108. The drug library and other databases may be stored on the MMU server 3108, on a separate server, and/or in remote locations.

Hospital information systems (HIS) 3110 may include one or more computers connected by cabling, interfaces, and/or Ethernet connections. Alternatively, wireless connections and communications may be used in whole or in part. Servers provide processing capability and memory for storage of data and various application programs or modules, including but not limited to an admissions-discharge-and-transfer (ADT) module or computer 3112, a computerized physician order entry (CPOE) module or computer 3114, and a pharmacy information system (PIS) module or computer 3116. Hospital personnel, such as admission clerks 3118, physicians 3120, and pharmacists 3122, respectively, may be authorized to access these modules through client workstations connected to the servers in order to enter data, access information, run reports, and complete other tasks.

In the embodiment shown in FIG. 1, the HIS 3110 may also include a POC system 3125 including a server or POC computer 3124 (sometimes referred to as a barcode point of care server or computer), or the POC computer 3124 may be separate from the HIS 3110. The POC computer 3124 may act as a part of the POC system 3125 (sometimes referred to as the barcode point of care system or BPOC) and may be able to wirelessly communicate through a plurality of wireless communication nodes located throughout the hospital, utilizing a wireless communications protocol, such as IEEE 801.11, IEEE 802.11, or Bluetooth. The POC computer 3124 may communicate wirelessly with a portable thick client, POC client 3126, carried by a caregiver. The POC client 3126 may be a personal digital assistant (PDA) that includes significant memory, display, and processing capabilities. The POC client device may execute a variety of programs stored in its memory in some degree independently of the POC computer 3124.

In one embodiment of FIG. 1, the MMU server 3108 may be hard-wired to the DLE client 3106 and to a MMU client 3128. Alternatively, the MMU and DLE client functions may be combined onto a single client computer/workstation or may reside together with the MMU server 3108 on a single combined MMU/DLE server. The MMU server 3108 may reside in a location remote from the patient's room or treatment area. For instance, the MMU server 3108 may reside in a secure, climate controlled information technology room with other hospital servers, and computer equipment and its client terminals may be located in the pharmacy, biomedical engineering area, nurse station, or ward monitoring area. One MMU server 3108 may monitor, coordinate, and communicate with many infusion pumps 3130. For example, in one embodiment, the MMU software running on the MMU server 3108 may support up to one thousand infusion pumps concurrently.

In embodiment of FIG. 1, the POC client 3126 in the POC system 3125 may communicate through the POC server 3124 with the MMU server 3108. The MMU server 3108 may interface or communicate wirelessly with the infusion pump 3130 through the same wireless nodes utilized by the POC system 3125 and a connectivity engine and antenna on or in the infusion pump 3130. Communication between the infusion pump 3130 and the POC client 3126 may take place through the MMU server 3108 and POC server 3124. The MMU server 3108 may store in an associated memory both the logical ID and the network ID or Internet Protocol (IP) address of the infusion pump(s) 3130, such that only the MMU server 3108 may communicate in a direct wireless manner with the infusion pump 3130. Alternatively, the MMU server 3108 may provide the IP address and other information about the infusion pump 3130 to the POC system 3125 to facilitate direct communication between the POC system 3125 and the infusion pump 3130.

Upon admission to the hospital, the admission clerk 3118 or similar personnel may enter demographic information about each patient 3104 into an associated memory of the ADT module or computer 3112 of an HIS database stored in an associated memory of the HIS 3110. Each patient 3104 may be issued a patient identification wristband, bracelet, or tag 112 that may include an identifier 3103, such as a barcode or RFID tag, identifying the patient. The wristband, bracelet, or tag 112 may also include other information, in machine readable or human-readable form, such as the name of the patient's doctor, blood type, allergies, and the like.

The patient's doctor 3120 may prescribe medical treatment by entering a medication order into the CPOE module or computer 3114 within the HIS 3110. The medication order may specify a start time, stop time, a range of allowable doses, physiological targets, route, and site of administration. In the case of an order for infusion of fluids or medication, the order may be written in various formats, and may include the patient's name, patient ID number, a unique medication order or prescription number, a medication name, medication concentration, a dose or dosage, frequency, and/or a time of desired delivery. This information may be entered into the memory of the CPOE module or computer 3114, and may be stored in a memory associated with at least the POC server 3124.

The medication order may also be delivered electronically to the PIS module or computer 3116 in the pharmacy and may be stored in an associated memory. The pharmacist 3122 may screen the prescribed order, translate it into an order for dispensing medication, and prepare the medication or fluids with the proper additives and/or necessary diluents. The pharmacist 3122 may prepare and affix a label 102 with drug container specific identifying information 3101 to the medication or drug container 3102. The label may include in machine-readable and/or human-readable form medical device specific delivery information including but not limited to the dispense ID number, patient ID, drug name, drug concentration, container volume, volume-to-be-infused ("VTBI"), rate, duration, and the like. Only two of the three variables VTBI, rate, and duration may be defined as the third may be calculated when the other two are known. The labeled medication may be delivered to a secure, designated staging location or mobile drug cart on the ward or floor near the patient's room or treatment area. The medication order pending dispensing or administration may be posted to a task list in the HIS 3110 and POC system 3125 and stored in an associated memory.

The caregiver 3132 (e.g., a nurse) may use the identification receiver 32 associated with the POC client 3126 to scan his/her caregiver identification badge 116 and enter a password, which logs the caregiver into the system and authorizes the caregiver to access a nurse's task list from the POC system 3125 through the POC client 3126. The caregiver 3132 may view from the task list that IV drugs are to be administered to certain patients 3104 in certain rooms. The caregiver 3132 obtains the necessary supplies, including medications, from the pharmacy and/or a staging area in the vicinity of the patient's room.

The caregiver 3132 may take the supplies to a patient's bedside, turn on the infusion pump 3130, verify that the network connection icon on the infusion pump 3130 indicates a network connection (for example, a wireless connection such as Wi-Fi or the like) is present, select the appropriate clinical care area (CCA) on the infusion pump 3130, and mount the IV bag, container, or vial 3102 and any associated tube set as required in position relative to the patient 3104 and infusion pump 3130 for infusion. Another connection icon on the infusion pump 3130 or pump user interface screen can indicate that a wired or wireless connection to the MMU server 3108 is present. Using the identification receiver/reader integral to the POC client 3126, the caregiver 3132 may scan the barcode on the patient's identification wristband, bracelet, or tag 112 or other patient identification device. A task list associated with that particular patient may appear on the POC client 3126 screen. The task list, which may also include orders to give other forms of treatment or medication by other routes (oral, topical, etc.), may be obtained from the HIS 3110 via the POC server 3124 and communicated wirelessly to the POC client 3126. In one embodiment, the list is generated by matching the scanned patient ID with the patient ID for orders in memory within the POC server 3124. In another embodiment, the order information may be obtained by scanning the drug container specific identification information for associated orders in memory within the POC server 3124, through the following step(s).

The caregiver 3132 may scan the medication barcode label 102 containing medication container specific identification information 3101 on the medication container 3102 with the POC client 3126. The POC client 3126 may highlight the IV administration task on the task list and send the scanned medication container specific identification information, such as dispense ID information, from the medication container 3102, to the POC server 3124. The POC server may use the medication container specific identification information to pull together the rest of the order details and send them back to the POC client 3126. The POC client 3126 may then display an IV Documentation Form on its screen. One side of the IV Documentation Form screen may show the order details as "ordered" and the other side may be reserved for a status report from the infusion pump 3130. The status report from the infusion pump 3130 may be transmitted to the POC client 3126 through the POC server 3124 and MMU server 3108. The lower portion of the IV Documentation Form screen may provide the caregiver 3132 with instructions (like to scan the infusion pump 3130 barcode) or identify whether the pump is running or stopped.

The caregiver 3132 may then scan the barcode label 92 associated with the infusion pump 3130 (or pump channel if the pump is a multi-channel pump). The barcode label 92 may contain medical device specific identification information 3131, such as the logical name and/or logical address of the device or channel. The POC system 3125 then automatically bundles the information into a program pump request containing the "order details" and in one embodiment, without further interaction with the caregiver 3132, transmits this information to the MMU server 3108.

The program pump request may include at least some of the following information (in HIS/POC system format): a Transaction ID, which may include a Logical Pump ID, a Pump Compartment, a Pump Channel ID, a Reference Device Address, a Caregiver ID, a Caregiver Name, a Patient/Person ID (HIS identifier), a Patient Name, a Patient Birth Date & Time, a Patient Gender, a Patient Weight, a Patient Height, and an Encounter ID which may include a Room, a Bed, and a Building (including CCA). The program pump request may also include Order Information or "order details", including an Order ID, a Start Date/Time, a Stop Date/Time, a Route of Administration, a Rate, a Duration of Infusion (Infuse Over), a Total Volume to be Infused (VTBI), an Ad Hoc Order Indicator, and Ingredients including HIS Drug Name or HIS Generic Drug Name, HIS Drug Identifier or HIS Generic Drug ID, Rx Type (Additive or Base), Strength w/units, and Volume w/units. The program pump request may further include Patient Controlled Analgesia (PCA) Orders Only information, such a PCA Mode-PCA only, Continuous only, or PCA and Continuous, a Lockout Interval (in minutes), a PCA Continuous Rate, a PCA Dose, a Loading Dose, a Dose Limit, a Dose Limit Time w/units, a Total Volume in vial or syringe, and Order Comments.

The MMU server 3108 may map or convert the wide range of expressions of units allowed by the HIS 3110 or POC system 3125 for POC client 3126 requests into the much more limited set of units allowed in the MMU server 3108 and infusion pump 3130. For example, the POC client 3126 request may express "g, gm, gram, or grams" whereas the MMU server 3108 and/or infusion pump 3130 may accept "grams" only. Infusion pump 3130 delivery parameters or infusion pump 3130 settings are mapped or converted from corresponding order information or "order details" of the program pump request.

The MMU server 3108 may store in an associated memory a mapping or translation table that keep track of the logical ID, serial number or other identifier of an infusion pump 3130 and the corresponding current network (static or dynamic) address (Internet Protocol (IP) address) or ID of the infusion pump 3130 on the network, which in this example is a wireless network. The MMU server 3108 may be able to translate or associate a given identifier of the infusion pump 3130 with its network address in the translation table and provide the network IP address to the requesting POC system 3125 or device. The MMU server 3108 may also store in an associated memory and/or look up the drug library applicable to the scanned infusion pump 3130 and/or convert the Drug ID and Strength from the pump program request into an index number of the medication at the desired strength or concentration from the drug library. The duration of the infusion may come from the POC system 3125 in hours and minutes and may be converted to just minutes for the infusion pump 3130 to recognize it. Volume or VTBI may be rounded to provide a value-specific and infuser-specific number of digits to the right of the decimal point. Units (of drug) may be converted to million units where appropriate. Patient weight may be converted and either rounded according to infuser-specific rules or not sent to the infuser.

Once the MMU server 3108 transforms the information from the program pump request into infusion pump settings or delivery parameters and other information in a format acceptable to the infusion pump 3130, the MMU server 3108 may wirelessly download a command message to the infusion pump 3130. If the infusion pump 3130 is not already equipped with the latest appropriate version of the hospital-established drug library, the MMU server 3108 may also automatically download a drug library to the infusion pump 3130. The hospital-established drug library may be maintained in a separate process undertaken by the biomedical engineer or pharmacist 3122 to place limits on the programming of the infusion pump 3130, as well as other infusion pump operating parameters such as default alarm settings for air in the line, occlusion pressure, and the like. The drug library may set up acceptable ranges or hard and/or soft limits for various drug delivery parameters in the infusion pump 3130.

The MMU server 3108 may also download to the infusion pump new versions, patches, or software updates of the infusion pump's internal operating system software. The infusion settings or delivery parameters and other information from the MMU server 3108 may be entered into the memory of the infusion pump 3130 and the infusion pump 3130 settings may automatically populate the programming screen(s) of the infusion pump 3130, just as if the caregiver 3132 had entered the information and settings manually. The infusion pump 3130 screen may populate with the name of the drug and drug concentration based on the drug library index number, patient weight, rate, VTBI, and/or duration. Further, the MMU server 3108 may detect that a new infusion pump has connected, determine whether the settings stored on the infusion pump are up to date, and/or transmit updated settings to the infusion pump as needed, as described in greater detail below with reference to FIGS. 2-7. A return message of confirmation signal may be sent to the MMU server 3108 by the infusion pump 3130 to indicate that the command message has been received. At this point, if necessary, the caregiver 3104 may manually enter any additional infusion settings or optional information that was not included in the command message.

The infusion pump 3130 may then prompt the caregiver 3132 to start the infusion pump 3130 by pressing the start button. When the caregiver 3132 presses the start button, a confirmation screen with the infusion settings programmed may be presented for confirmation and an auto-program acknowledgment message can be sent to the MMU server 3108 to forward without request (i.e., pushed in a near real-time manner) or provide to the POC system 3125 when requested or polled. When the caregiver 3132 presses the button to confirm, the infusion pump 3130 may begin delivering fluid according to the programmed settings. The infusion pump 3130 may send a status message to the MMU server 3108 indicating that the infusion pump 3130 was successfully auto-programmed, confirmed and started by the caregiver 3132, and is now delivering fluid. This information may also be displayed at the infusion pump. The MMU server 3108 may continue to receive logs and status messages wirelessly from the infusion pump 3130 periodically as the infusion progresses or when alarms occur.

The MMU server 3108 may report a portion of the initial status message to the POC client 3126 through the POC server 3124 (in MMU format) to indicate that the infusion pump 3130 has been auto-programmed and the caregiver 3132 has confirmed the settings. The MMU server 3108 may communicate to the POC system 3125 and/or at the infusion pump 3130 the actual Rate, VTBI, and Duration. A notation at the bottom of the screen of the POC client and/or the infusion pump may indicate that the infusion pump 3130 is running. The infusion pump 3130 may compare and give a visual, audio, or other type of affirmative signal if the pump information matches or acceptably corresponds with the ordered information. An initial determination of whether the pump information matches the order may be done in the MMU server 3108 and communicated to the POC client 3126 through the POC server 3124. Alternatively, the POC server 3124 or the infusion pump 3130 may make the necessary comparisons. If the pump information does not match the order, the infusion pump 3130 at the display 88 may output a visual, audio, or other type of negative signal, which may include an error message.

The caregiver 3132 may be prompted to review and press a save button on the infusion pump 3130 if the order has been begun as desired or any variations are acceptable. The MMU server 3108 may receive status, event, differences, and variation information from the infusion pump 3130 and pass such information to the POC system 3125. In a separate subsequent step, the nurse may electronically sign the record and presses a send button on the POC client POC client 3126 to send the information to the patient's electronic medication record (EMR) or medication administration record (MAR).

Other Environments

FIG. 1 illustrates one example environment in which the various medical device reconfiguration techniques of the present disclosure may be utilized. However, the embodiments described herein are not limited to such an environment, and may be applied to any network environment including one or more servers in which medical devices in different geographical regions use different sets of settings. An example system that may be implemented in one or more of such network environments to provide location-based medical device reconfiguration is described below with reference to FIG. 2.

System Overview

Figure 2:
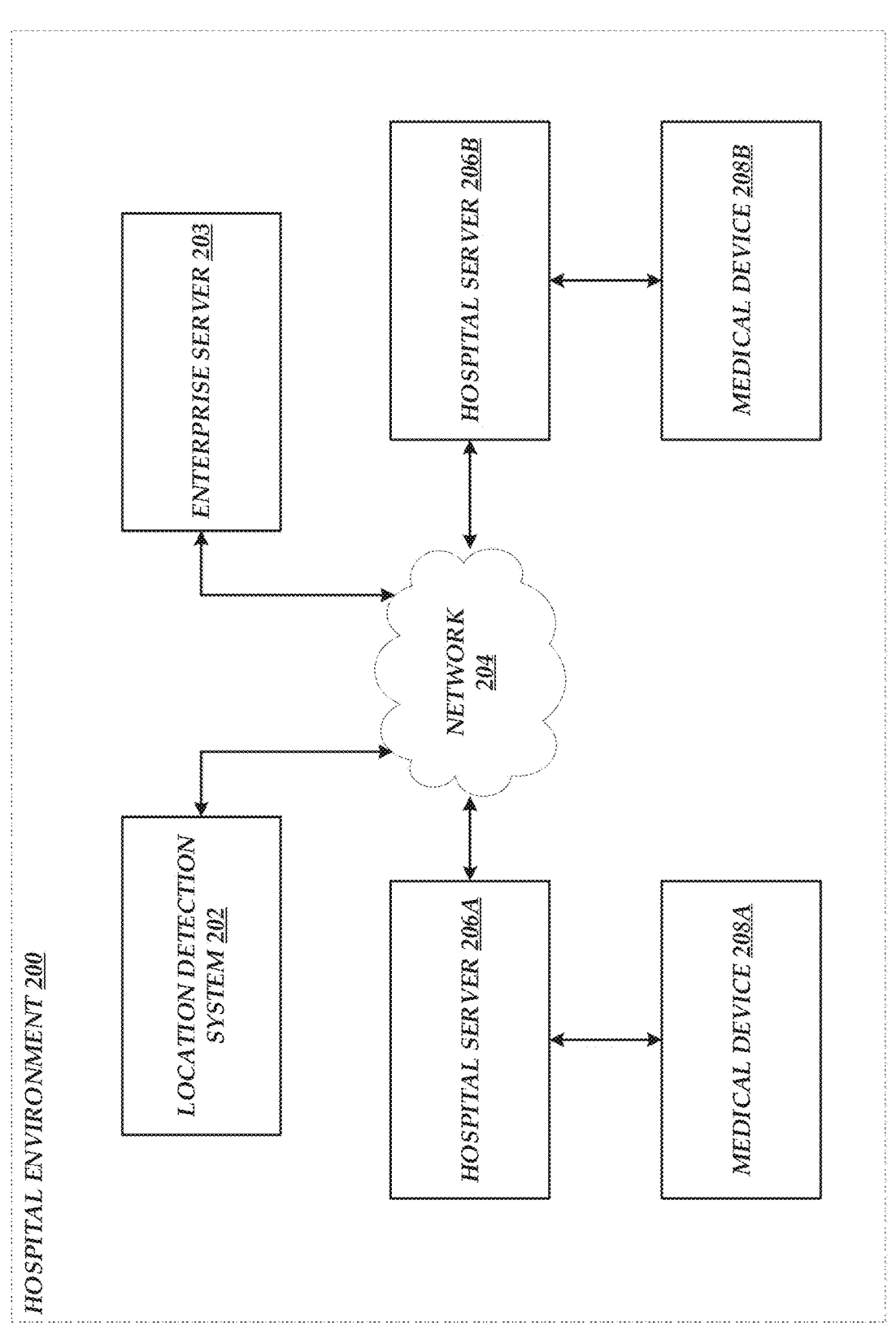
FIG. 2 is a block diagram illustrating components of an example hospital environment in accordance with aspects of the present disclosure.

FIG. 2 is a block diagram of an example hospital environment 200, which includes an arrangement of computer hardware and software components that may be used to implement aspects of the present disclosure. The hospital environment 200 may include many more (or fewer) elements and/or sub-elements than those shown in FIG. 2. It is not necessary, however, that all of these elements be shown in order to provide an enabling disclosure. As illustrated in FIG. 2, the hospital environment 200 includes a location detection system 202, an enterprise server 203, a hospital server 206A, and a hospital server 206B connected to a network 204, and additionally, a medical device 208A in communication with the hospital server 206A, and a medical device 208B in communication with the hospital server 206B. Although only two hospital servers and two medical devices are shown in FIG. 2, the hospital environment 200 may, in some embodiments, include only a single hospital server or more than two hospital servers. Additionally or alternatively, one or more of the hospital servers in the hospital environment 200 may include two or more medical devices.

Location Detection System

The location detection system 202 may use Global Navigation Satellite System (GNSS), such as Global Positioning System (GPS) or GLONASS navigation system, for geospatial positioning, and/or non-GNSS technologies such as Pedestrian Dead Reckoning (PDR), inertial navigational systems, magnetic positioning systems, and the like. In some embodiments, the location detection system 202 uses existing wireless technologies to perform geo-positioning, which may include Wi-Fi-based positioning systems (WPS), Bluetooth-based positioning systems, Radio-Frequency Identification (RFID) systems, and others. In other embodiments, the location detection system may include video processing systems, ultrasound-based systems, visible light communication systems, and so forth.

The location detection system 202 can allow geo-fences to be drawn on a map and notify the enterprise server 203 when a medical device crosses the geo-fences (e.g., when the medical device enters a geo-fenced area, exits a geo-fenced area, or both). If a hospital administrator wishes to take certain actions (e.g., track the locations of medical devices, reconfigure the settings on medical devices, etc.) in response to medical devices entering or exiting specific areas of the hospital (e.g., rooms, floors, wings, buildings, or clinical care areas such as emergency room, operating room, intensive care unit, etc.), he or she may configure the location detection system 202 to monitor movements of medical devices across the boundaries of such areas. In response to the notification from the location detection system 202 that a medical device has entered a designated geo-fenced area, the enterprise server 203 may transmit further instructions, for example, to the hospital server in communication with the medical device. In some embodiments, the medical device determines its own location (e.g., using a tag or a tracking device built into the medical device) and communicates its location or any other associated information (e.g., an identifier associated with the geo-fenced area in which the medical device is located) to one or more of the location detection system 202, the enterprise server 203, or the hospital server. In some embodiments, one or more of the location detection system 202, the enterprise server 203, or the hospital server determine, estimate, or derive the location of the medical device from the IP address of the medical device (e.g., using netmask and/or a map of access points within the hospital facility). In such embodiments, the location of the medical device can be determined, estimated, or derived using existing hardware (e.g., for implementing IEEE 802.X protocols) and maps (e.g., map of access points established on the hospital server), and the expense and complexity associated with implementing a traditional location system can be avoided or reduced.

In some embodiments, the location detection system 202 also detects how the medical devices entered or exited a geo-fenced area, and different actions may be triggered depending on the manner in which the medical device has entered or exited the geo-fenced area.

For example, the enterprise server or the hospital server may take one action if an infusion pump exited the hospital through the front door and another action if the infusion pump exited on an ambulance.

Dwell Time in Location Detection

In some embodiments, the location detection system 202 does not send a location change notification to the enterprise server 203 (or a hospital server) unless the location change holds at least a threshold amount of time. For example, an infusion pump may be traveling from geo-fenced area A, through geo-fenced area B, to geo-fenced area C (which may correspond to three different rooms, floors, clinical care areas, wings, buildings, etc.). The location detection system 202 may detect the location change from area A to area B, but based on the amount of time that the infusion pump spent in area B being less than 5 minutes, the location detection system may refrain from sending a notification to the enterprise server. Once the infusion pump arrives at area C, based on the amount of time that the infusion pump spent in area C being greater than or equal to 5 minutes, the location detection system may send a notification to the enterprise server that the location of the infusion pump has changed from area A to area C.

Additionally or alternatively, the location detection system 202 may not send a location change notification to the enterprise server 203 (or a hospital server) unless the medical device is stationary for at least a threshold amount of time. For example, an infusion pump may be traveling from geo-fenced area A, through geo-fenced area B, to geo-fenced area C (which may correspond to three different rooms, floors, clinical care areas, wings, buildings, etc.). The location detection system 202 may detect the location change from area A to area B, but based on the fact that the infusion pump is continuously moving (or remaining stationary for less than the threshold amount of time) in area B, the location detection system may refrain from sending a notification to the enterprise server. Once the infusion pump arrives at area C, based on the infusion pump remaining stationary for at least the threshold amount of time in area C, the location detection system may send a notification to the enterprise server that the location of the infusion pump has changed from area A to area C.

Enterprise Server

The enterprise server 203 may be a server in charge of the entire hospital or enterprise that can communicate with all hospital servers in the hospital or enterprise (e.g., the hospital environment 200). The enterprise server 203 may send instructions to the location detection system 202 to identify the medical devices that the location detection system 202 should monitor and to define the gen-fencing boundaries that the enterprise server 203 should be notified about. In response to a notification from the location detection system 202 indicating that a monitored medical device has entered a new geo-fenced area, the enterprise server 203 may take certain designated actions such as log the location change of the medical device, instruct the hospital server connected to the medical device to update the settings on the medical device, and the like. In some embodiments, the enterprise server 203 is omitted, and the location detection system 202 communicates directly with one or more of the hospital servers in the hospital environment 200.

In some embodiments, the enterprise server 203 (or the hospital server if location change notification is sent directly to the hospital server) may determine whether the location detection system 202 is an authorized, authenticated service prior to initiating any location-based actions described herein. The enterprise server 203 may utilize OAuth or another authorization protocol such as a public/private key certificate exchange.

Network

The network 204 may be any wired network, wireless network, or combination thereof. In addition, the network 204 may be a personal area network, local area network, wide area network, over-the-air broadcast network (e.g., for radio or television), cable network, satellite network, cellular telephone network, or combination thereof. For example, the network 204 may be a publicly accessible network of linked networks such as the Internet. For example, the communications between the location detection system 202 and the enterprise server 203 may be over a publicly accessible network of linked networks such as the Internet, and the communications between the enterprise server 203 and the hospital servers 206A and 206B (and also the communications between the hospital server 206A and the medical device 208A, and the communications between the hospital server 206B and the medical device 208B) may be implemented on one or more wired and/or wireless private networks. The enterprise server 203 may be a cloud server that includes a collection of services, which are delivered via the network 204 as web services.

Hospital Server

The hospital servers 206A and 206B may each represent a version of the MMU server 3108 described with reference to FIG. 1. For example, the hospital server 206A may communicate with the medical devices in Hospital A (e.g., update settings on medical devices, send commands to medical devices to initiate or stop clinical operations, and the like), and the hospital server 206B may communicate with the medical devices in Hospital B that is separate from Hospital A (but may belong to the same hospital network or enterprise as Hospital A).

Medical Device

The medical devices 208A and 208B may be any medical device that are mobile and can be moved across the geo-fences monitored by the location detection system 202. For example, the medical devices 208A and 208B can be infusion pumps, patient monitors, and the like. The medical devices 208A and 208B are described in greater detail below with reference to FIG. 3.

Figure 3:
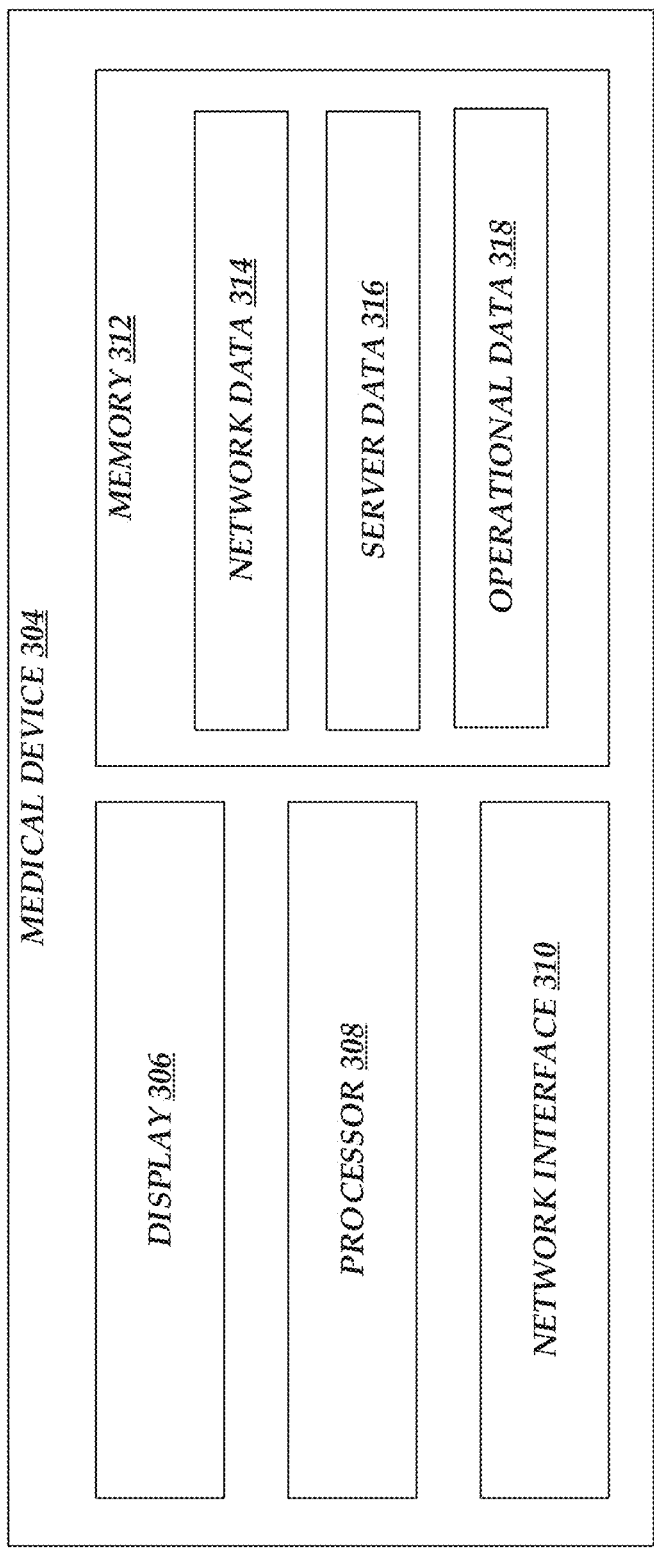
FIG. 3 is a block diagram illustrating a general architecture of an example medical device in accordance with aspects of this disclosure.

With reference to FIG. 3, the components of an example medical device are described in greater detail. The example architecture of the medical devices 208A and 208B depicted in FIG. 2 includes an arrangement of computer hardware and software modules that may be used to implement aspects of the present disclosure. The medical device 304 may include many more (or fewer) elements and/or sub-elements than those shown in FIG. 3. It is not necessary, however, that all of these elements be shown in order to provide an enabling disclosure.

As illustrated, the medical device 304 includes a display 306, a processor 308, a network interface 310, and a memory 312, all of which may communicate with one another by way of a communication bus. The display 306 may display information generated or stored by the medical device 304 or any other information associated with the medical device 304. For example, the medical device may be an infusion pump being used to deliver medication to a patient. In such a case, the display 306 may display the volume of the medication infused so far, the volume of the medication to be infused, the rate at which the medication is being infused, and the like. The processor 308 may receive information and instructions from other computing systems or services via a network. The processor 308 may also transmit information to and receive information from the memory 312 and further provide content to the display 306 for display. The network interface 310 may provide connectivity to one or more networks or computing systems in the network environment described herein. For example, the network interface 310 may be a serial port, a parallel port, or any other communication interface that can enable or facilitate wired or wireless communication according to any communication protocols such as Zigbee (e.g., IEEE 802.15.4), Bluetooth, Wi-Fi (e.g., IEEE 802.11), Near Field Communication (NFC), and the like.

The memory 312 may contain computer program instructions (grouped as modules in some embodiments) that the processor 308 can execute in order to implement one or more aspects of the present disclosure. The memory 312 may include RAM, ROM, and/or other persistent, auxiliary, or non-transitory computer-readable media. In some embodiments, the memory 312 stores an operating system that provides computer program instructions for use by the processor 308 in the general administration and operation of the medical device 304. As illustrated in FIG. 3, the memory 312 may include network data 314, server data 316, and operational data 318. In some embodiments, the medical device 304 uses the network data 314 to connect to a network in the hospital environment (e.g., Wi-Fi network), uses the server data 316 to connect to a hospital server in the hospital environment (e.g., MMU server 3108 of FIG. 1), and uses the operational data 318 to perform one or more clinical operations (e.g., initiate an infusion therapy on a patient). In some embodiments, the operational data may also referred to herein as clinical data or clinical settings.

Although not shown in FIG. 3, the memory 312 may store programs, instructions, modules, libraries, settings, parameters, and/or other types of data that may be used by the medical device 304 to perform its operations. For example, the memory 312 may store location data indicating the current location of the medical device 304. Such location data may be updated in response to the change in the location of the medical device 304, and transmitted to the hospital server and/or the enterprise server for monitoring and logging purposes (e.g., such that various location-based metrics such as device utilization can be generated based on how long the individual medical devices spend in which geographical areas such as hospital rooms, cleaning stations, specific clinical care areas, specific buildings and facilities, etc.).

As another example, the memory 312 may store network profiles for multiple networks that may be used by the medical device 304 to connect to any of such networks.

Additionally or alternatively, the memory 312 may store server profiles for multiple hospital servers that may be used by the medical device 304 to connect to any of such hospital servers. In such cases, the enterprise server and/or the hospital server described herein may first determine whether the medical device 304 already stores the network profile and/or the server profile associated with the newly-entered geographical area prior to providing such information to the medical device 304. Based on the medical device 304 already storing such information, the enterprise server and/or the hospital server may refrain from sending such information to the medical device 304. Based on the medical device 304 not already storing any portion of such information, the enterprise server and/or the hospital server may send such portion of the information to the medical device 304. In other embodiments, the medical device 304 may be configured to only one network profile and/or only one server profile at a time, and the enterprise server and/or the hospital server may provide the network/server information associated with the newly-entered geographical without such determination.

Although the present disclosure describes reconfiguring the settings on medical devices, the embodiments described herein are not limited as such, and the techniques described herein can be applied to any type of data (e.g., programs, instructions, modules, libraries, settings, parameters, and/or other types of data) that is location-specific and may need to be updated in response to the location of the medical devices being changed.

Although not shown in FIG. 3, the medical device 304 may further include one or more input devices such as a touch screen, mechanical buttons, or a voice recognition system. Also, the medical device 304 may include any other number of components such as multiple displays, multiple processors, multiple network interfaces, and/or multiple memories. Further, the medical device 304 may include one or more additional storage devices for storing data generated by the medical device 304 or other data utilized in implementing aspects of the present disclosure.

Movement of Medical Device Across Geographical Areas

Figure 4:
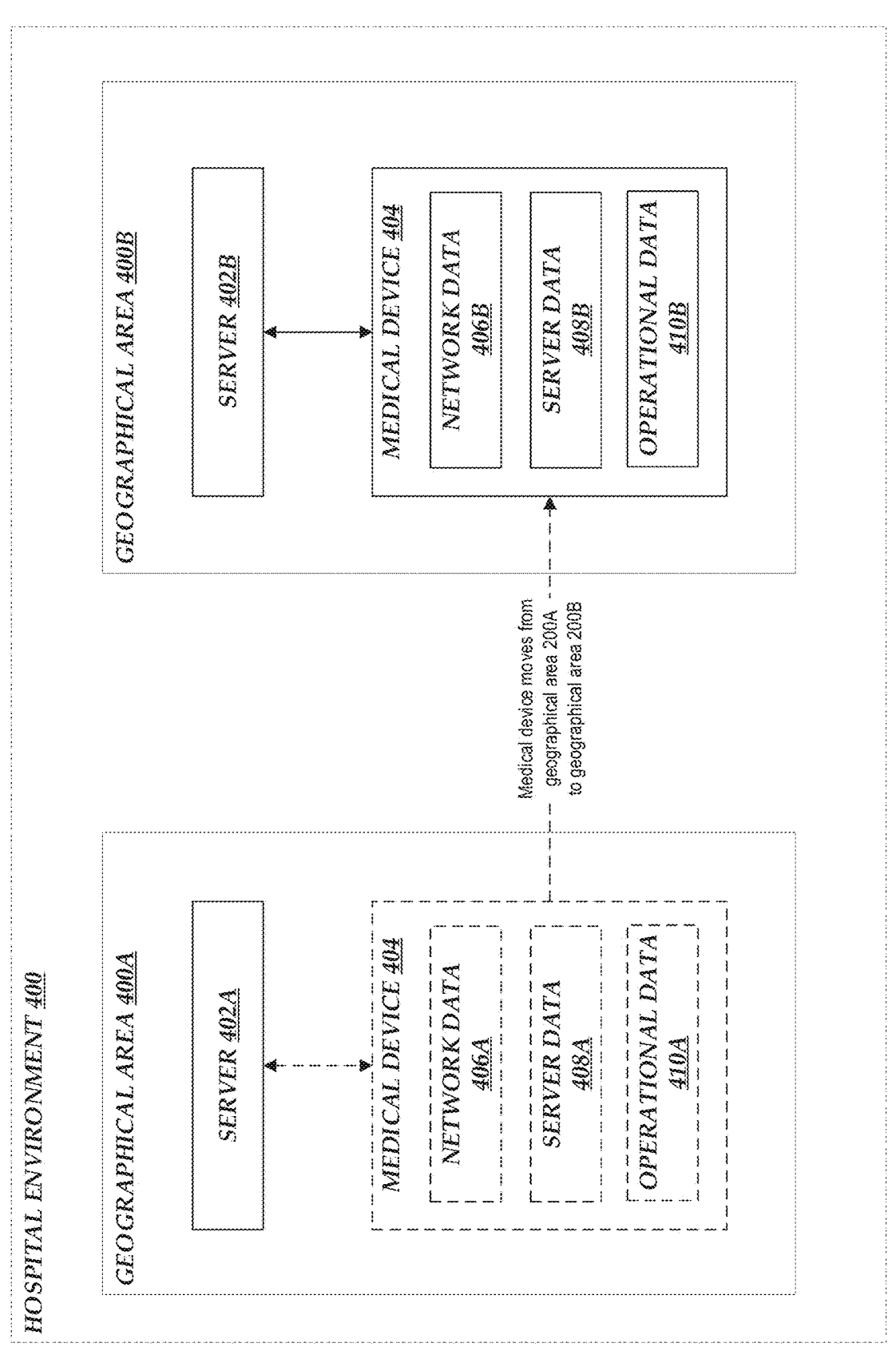
FIG. 4 a block diagram illustrating movement of a medical device across geographical areas in an example hospital environment in accordance with aspects of this disclosure.

With reference now to FIG. 4, an example hospital environment 400 will be described. The hospital environment 400 includes a geographical area 400A (e.g., geo-fence A) including a server 402A and a geographical area 400B (e.g., geo-fence B) including a server 402B. Although the servers 402A and 402B are illustrated as being located within the geographical areas 400A and 400B, respectively, in some embodiments, one or both of the servers 402A and 402B are located outside the corresponding illustrated geographical area.

As shown in FIG. 4, a medical device 404 including network data 406A, server data 408A, and operational data 410A was previously in the geographical area 400A and connected to the server 402A. The medical device 404 is then moved to the geographical area 400B. In response to detecting that the medical device 404 has entered the geographical area 400B, a location detection system (e.g., location detection system 202 of FIG. 2) may transmit a notification to an enterprise server (e.g., enterprise server 203 of FIG. 2) or the server 402A, indicating that the medical device 404 has entered the geographical area 400B, which is associated with a different server, server 402B. In response to the notification, the server 402A may provide updated network data 406B and server data 408B to the medical device 404 (e.g., over an existing wireless network connection established between the server 402A and the medical device 404). The medical device 404 may connect to the wireless network available in the geographical area 400B using the received updated network data 406B, and connect to the server 402B using the received updated server data 408B. In response to determining that the medical device 404 has operational data 410B that is incompatible with the geographical area 400B, the server 402B may transmit updated operational data 410B to the medical device 404. While the medical device is located in the geographical area 400B, the medical device 404 may perform clinical operations using the updated operational data 410B. The medical device reconfiguration process is described in greater detail below with reference to FIG. 5.

Although all of the network data, server data, and operational data are updated in the example of FIG. 4, in some embodiments, only one or some of the data stored on the medical device 404 may be updated in response to a location change of the medical device. For example, if the medical device 404 is moved to a different geo-fenced area that is managed by the same hospital server to which the medical device 404 is already connected, the server data may not need to be updated since the medical device 404 can continue to communicate with the same hospital server in the new geo-fenced area. As another example, if the medical device 404 is moved to a different geo-fenced area that is still part of the same wireless network to which the medical device 404 is already connected, the network data may not need to be updated since the medical device 404 can continue to access the same wireless network in the new geo-fenced area. As another example, if the medical device 404 is moved to a different geo-fenced area that uses the same operational data (e.g., drug library version, safety parameters, etc.) as the geo-fenced area in which the medical device 404 was previously located, the operational data may not need to be updated since the medical device 404 can continue to use the same operational data to perform its clinical operations in the new geo-fenced area.

Medical Device Reconfiguration Process

Figure 5:
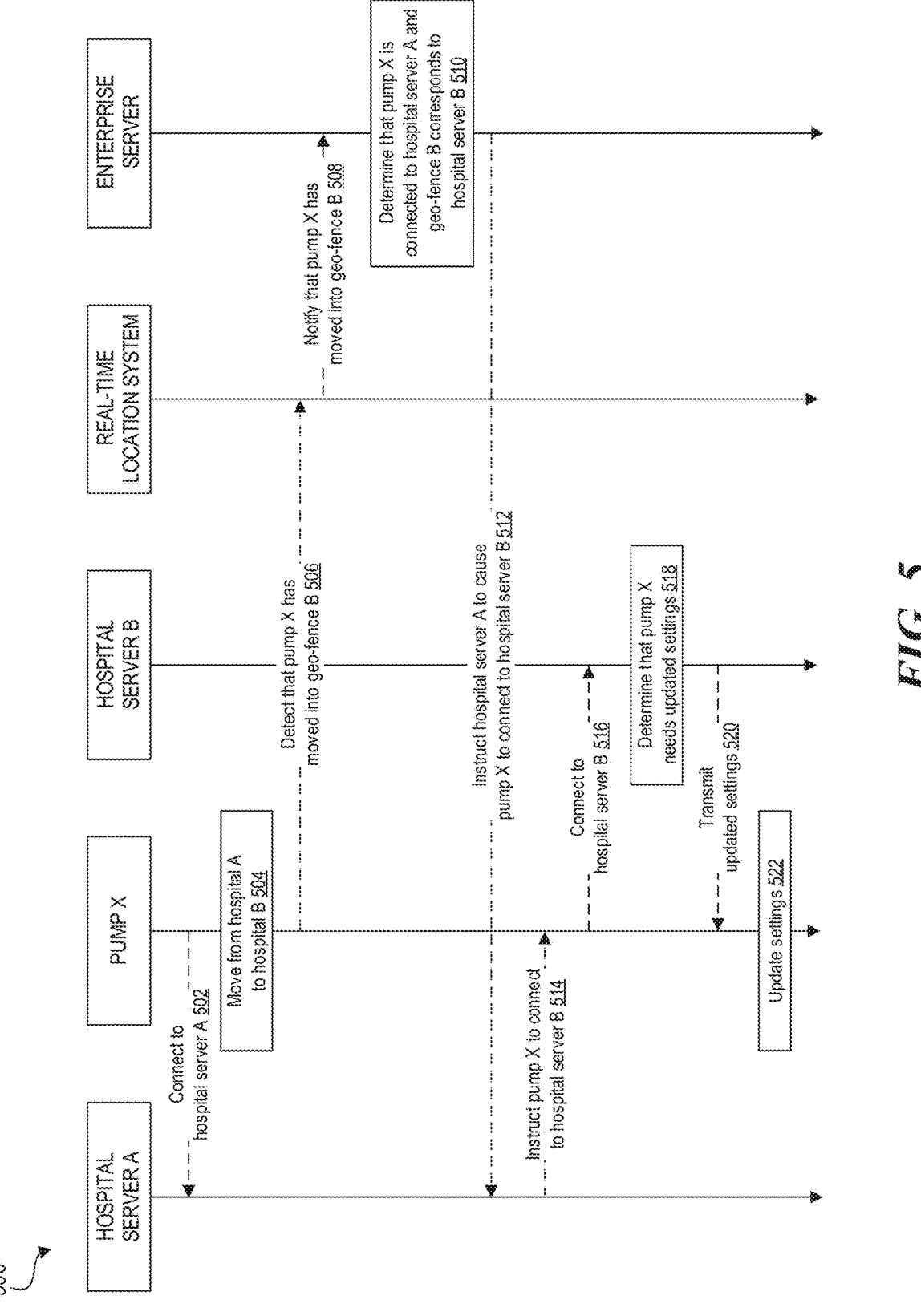
FIG. 5 is a process flow diagram illustrating the interactions among various components in an example hospital environment in accordance with aspects of this disclosure.

With reference now to FIG. 5, an example medical device reconfiguration process 500 will be described. At step 502, pump X connects to hospital server A. When the infusion pump connects to the hospital server for the first time, the hospital server may check the settings on the infusion pump (e.g., network settings, server settings, safety settings, drug library versions, etc.) and cause some or all of the settings on the infusion pump to be updated as needed (e.g., by transmitting updated settings to the infusion pump). The same process of ensuring that the medical device has the latest settings and versions may be repeated the next time the infusion pump connects to the hospital server. In some embodiments, after the first time, the hospital server may omit one or more of the steps performed to ensure that the medical device has the latest settings and versions (e.g., based on how long ago the medical device last connected to the hospital server).

At step 504, pump X is moved from hospital A (managed by hospital server A) to hospital B (managed by hospital server B). For example, the infusion pump connected to a patient admitted at hospital A may have been transported to hospital B along with the patient.

At step 506, the real-time location system (RTLS) detects that pump X has moved into geo-fence B that has been defined at hospital B. For example, as pump X is moved into geo-fence B, a detector or receiver located at hospital B may detect the presence of pump X within the geo-fence B. As discussed with reference to FIG. 2, the RTLS may utilize any of a variety of location detection technologies to detect the location change of pump X. As part of the detection process, the RTLS may determine an identifier associated with pump X (e.g., ID of a location detection tag attached to pump X, or ID of pump X).

At step 508, the RTLS transmits a notification to the enterprise server, indicating that pump X has moved into geo-fence B. The notification may include the identifier associated with pump X determined at step 506 and an identifier associated with geo-fence B.

At step 510, the enterprise server determines that pump X is connected to hospital server A and geo-fence B corresponds to hospital server B. For example, the enterprise server determines the identity of pump X using the identifier associated with pump X included in the notification, and determines the identity of hospital server B using the identifier associated with geo-fence B included in the notification. The enterprise server may maintain and/or access a database table associating the location detection tags with the respective pumps, and determine the identity of pump X using the database table. Similarly, the enterprise server may maintain and/or access a database table associating the geo-fenced areas monitored by the RTLS with the respective hospital servers, and determine the identity of hospital server B using the database table.

At step 512, the enterprise server instructs hospital server A to cause pump X to connect to hospital server B. In some embodiments, only the hospital server (and not other hospital servers) connected to the infusion pump may be able to communicate with and send instructions to the infusion pump. The enterprise server may provide to hospital server A certain information that pump X would need in order to connect to hospital server B, such as network settings (e.g., SSID and pre-shared key) to connect to the Wi-Fi network at hospital B, server settings (e.g., the IP address of hospital server B) to connect to hospital server B over the network at hospital B, and other information such as a security certificate to communicate with the hospital server B over the network at hospital B.

At step 514, hospital server A instructs pump X to connect to hospital server B. For example, hospital server A may identify pump X using the identifier received from the enterprise server, and send a command to pump X including the information provided by the enterprise server (e.g., network settings, server settings, etc.). In some embodiments, the enterprise server provides the identifier of pump X and the identifier of hospital server B, and hospital server A determines the network settings, server settings, and other information that pump X would need in order to connect to hospital server B based on the identifiers provided by the enterprise server. Hospital server A then transmits such information to pump X.

At step 516, pump X connects to hospital server B. For example, in response to the communication from hospital server A, pump X connects to the Wi-Fi network at hospital B, and then connects to hospital server B over the Wi-Fi network using the IP address received from hospital server A.

At step 518, hospital server B detects that pump X has connected and determines that pump X needs updated operational settings (e.g., drug library, safety parameters, etc.). For example, hospital B may have stricter safety protocols and have tighter drug library limits for performing infusion therapies.

At step 520, hospital server B transmits updated settings to pump X, and at step 522, the settings on pump X are updated based on the updated settings received from hospital server B.

In the process 500, one or more of the steps shown in FIG. 5 may be removed (e.g., not performed) and/or the order in which the method 500 is performed may be switched. In some embodiments, additional steps may be added to the process 500. Although the process 500 is described in the context of updating the settings on an infusion pump, the techniques described herein can be extended to updating other types of data on other types of medical devices. The embodiments of the present disclosure are not limited to or by the example shown in FIG. 5, and other variations may be implemented without departing from the spirit of this disclosure.

Example Multi-Server Medical Device Reconfiguration Method

With reference now to FIG. 6, an example multi-server medical device reconfiguration method 600 will be described. The example method 600 may be carried out, for example, by the MMU server 3108 of FIG. 1, the hospital server 206A of FIG. 2, or the server 402A of FIG. 4 (or one or more components thereof). For convenience, the steps of the example method 600 are described as being performed by a server. The method 600 illustrates an example algorithm that may be programmed, using any suitable programming environment or language, to create machine code capable of execution by a CPU or microcontroller of the server. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory of the server that is coupled to the CPU or microcontroller and then then executed by the CPU or microcontroller.

At block 602, the server receives a request to connect from a medical device. The medical device may be an infusion pump connecting to the server at the hospital in which the infusion pump is located.

At block 604, the server transmits a first set of clinical settings to the medical device. For example, in response to detecting that the medical device has connected and determining that the medical device needs an updated drug library or updated safety parameters, the server can transmit such information to the medical device.

At block 606, the server determines that the medical device has performed a clinical operation using at least part of the clinical settings. For example, using the updated drug library or updated safety settings, the medical device may perform an infusion therapy on patient (e.g., in response to a command received from the server) and report to the server that the infusion therapy has been initiated (or completed). In some cases, the infusion therapy may be defined by certain parameters that may not have been allowed under the safety settings stored on the medical device prior to block 604.

At block 608, the server determines that the medical device has entered another geographical region associated with a remote server. For example, the server can make such a determination based on a notification received from the location detection system 202 (e.g., directly from the location detection system 202 or indirectly via the enterprise server 203).

At block 610, the server transmits, to the medical device, one or more settings usable by the medical device to connect to the remote server. For example, such settings may include network settings (e.g., SSID and pre-shared key) to connect to the Wi-Fi network in the new geographical region, server settings (e.g., the IP address) to connect to the remote server over the network at the new geographical region, and/or other information such as a security certificate to communicate with the remote server over the network at the new geographical region. Although not shown in FIG. 6, the server may terminate the network connection to the medical device in response to the medical device establishing a network connection to the remote server (or sometime thereafter).

In the method 600, one or more of the blocks shown in FIG. 6 may be removed (e.g., not performed) and/or the order in which the method 600 is performed may be switched. In some embodiments, additional blocks may be added to the method 600. The embodiments of the present disclosure are not limited to or by the example shown in FIG. 6, and other variations may be implemented without departing from the spirit of this disclosure.

Example Single-Server Medical Device Reconfiguration Method

With reference now to FIG. 7, an example single-server medical device reconfiguration method 700 will be described. The example method 700 may be carried out, for example, by the MMU server 3108 of FIG. 1, the hospital server 206A of FIG. 2, or the server 402A of FIG. 4 (or one or more components thereof). For convenience, the steps of the example method 700 are described as being performed by a server. The method 700 illustrates an example algorithm that may be programmed, using any suitable programming environment or language, to create machine code capable of execution by a CPU or microcontroller of the server. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory of the server that is coupled to the CPU or microcontroller and then then executed by the CPU or microcontroller.

At block 702, the server receives an indication from a location detection system that a medical device has entered a geographical area. For example, the server can make such a determination based on a notification received from the location detection system 202 (e.g., directly from the location detection system 202 or indirectly via the enterprise server 203). The geographical area may be a different clinical care area that is still managed by the same server and may include updated safety settings that are specific to the that clinical care area.

At block 704, the server determines that the location detection system is authorized. For example, the server (e.g., the enterprise server or the hospital server) may determine whether the location detection system is an authorized, authenticated service prior to initiating any location-based actions described herein. The server may utilize OAuth or another authorization protocol such as a public/private key certificate exchange.

At block 706, the server transmits an instruction to the medical device to update one or more of the settings stored on the medical device. In some embodiments, the settings are updated in response to the instruction transmitted from the server without further user approval. In other embodiments, the settings are updated only after a human operator (e.g., the clinician operating the medical device) approves the update via the user interface provided by the medical device (e.g., by hitting the confirm key after viewing the proposed update displayed on the display of the medical device).

At block 708, the server determines that the medical device has performed a clinical operation based on at least part of the update settings. For example, using the updated drug library or updated safety settings specific to the new geographical area (e.g., new clinical care area), the medical device may perform an infusion therapy on patient (e.g., in response to a command received from the server) and report to the server that the infusion therapy has been initiated (or completed). In some cases, the infusion therapy may be defined by certain parameters that may not have been allowed under the old settings previously stored on the medical device prior to block 706.

In the method 700, one or more of the blocks shown in FIG. 7 may be removed (e.g., not performed) and/or the order in which the method 700 is performed may be switched. In some embodiments, additional blocks may be added to the method 700. The embodiments of the present disclosure are not limited to or by the example shown in FIG. 7, and other variations may be implemented without departing from the spirit of this disclosure.

Example Embodiments

In one embodiment, a system configured to update medical device settings includes: a location detection system configured to monitor location information associated with a plurality of medical devices; a first server configured to update configuration information stored on one or more medical devices in a first geographical region; and a second server configured to update configuration information stored on one or more medical devices in a second geographical region different from the first geographical region, wherein the location detection system is further configured to: determine that a first medical device has entered the second geographical region, the first medical device including a first set of network settings usable to communicate with the first server and a first set of clinical settings usable to perform clinical operations in the first geographical region; and transmit an indication to the first server that the first medical device has entered the second geographical region, wherein the first server is further configured to: in response to the indication that the first medical device has entered the second geographical region, transmit, to the first medical device, a second set of network settings usable to communicate with the second server, and wherein the second server is further configured to: in response to a connection request from the first medical device, determine that the first set of clinical settings stored on the first medical device need to be updated; and transmit, to the first medical device, a second set of clinical settings usable to perform clinical operations in the second geographical region.

In one embodiment, the second server is further configured to transmit an instruction to the first medical device to initiate an infusion therapy to a patient in the second geographical region using the second set of clinical settings. In one embodiment, the first server is further configured to, in response to a connection request from the first medical device, determine that the second set of clinical settings stored on the first medical device need to be updated, and transmit, to the first medical device, the first set of clinical settings previously stored on the first medical device. In one embodiment, the first server is further configured to transmit, along with the second set of network settings, a Wi-Fi setting usable by the first medical device to connect to a Wi-Fi network associated with the second server.

In one embodiment, a server configured to update configuration information stored on one or more medical devices in a first geographical region, is further configured to: receive a request to connect to the server from a medical device configured to perform clinical operations; transmit, to the medical device, a first set of clinical settings usable to perform the clinical operations in the first geographical region; determine that the medical device has performed a clinical operation in the first geographical area using at least part of the first set of clinical settings; determine that the medical device has entered a second geographical area associated with a remote server configured to update configuration information stored on one or more medical devices in the second geographical region, wherein the second geographical area is different from the first geographical area; and transmit one or more settings to the medical device that are usable by the medical device to connect to the remote server.

In one embodiment, the server is further configured to, prior to transmitting the first set of settings to the medical device, determine that the medical device does not have at least some of the first set of settings usable to perform the clinical operations in the first geographical region. In one embodiment, the server is further configured to transmit an instruction to initiate an infusion therapy to a patient in the first geographical area. In one embodiment, the server is further configured to, subsequent to transmitting the one or more settings to the medical device, determine that the medical device is no longer connected to the server. In one embodiment, the server is further configured to determine that the medical device has entered the second geographical area associated with the remote server based on a notification generated by a location detection system configured to detect that the medical device has entered the second geographical area. In one embodiment, the server is further configured to, subsequent to transmitting the one or more settings to the medical device, receive another request to connect to the server from the medical device, and transmit the first set of clinical settings to the medical device based on a determination that the medical device does not have the first set of clinical settings.

In one embodiment, the server is further configured to, subsequent to transmitting the one or more settings to the medical device, receive another request to connect to the server from the medical device, and refrain from transmitting the first set of clinical settings to the medical device based on a determination that the medical device already has the first set of clinical settings. In one embodiment, the one or more settings transmitted to the medical device comprise a Wi-Fi setting usable by the medical device to connect to a Wi-Fi network associated with the remote server.

In one embodiment, a method of updating configuration information stored on one or more medical devices in a first geographical region comprises: receiving a request to connect to the server from a medical device configured to perform clinical operations; transmitting, to the medical device, a first set of clinical settings usable to perform the clinical operations in the first geographical region; receiving an indication that the medical device has performed a clinical operation in the first geographical area using at least part of the first set of clinical settings; receiving an indication that the medical device has entered a second geographical area associated with a remote server configured to update configuration information stored on one or more medical devices in the second geographical region, wherein the second geographical area is different from the first geographical area; and transmitting one or more settings to the medical device that are usable by the medical device to connect to the remote server.

In one embodiment, the method further comprises, prior to transmitting the first set of settings to the medical device, determining that the medical device does not have at least some of the first set of settings usable to perform the clinical operations in the first geographical region. In one embodiment, the method further comprises, transmitting an instruction to initiate an infusion therapy to a patient in the first geographical area. In one embodiment, the method further comprises, subsequent to transmitting the one or more settings to the medical device, determining that the medical device is no longer connected to the server.

In one embodiment, the method further comprises, determining that the medical device has entered the second geographical area associated with the remote server based on a notification generated by a location detection system configured to detect that the medical device has entered the second geographical area. In one embodiment, the method further comprises, subsequent to transmitting the one or more settings to the medical device, receiving another request to connect to the server from the medical device, and transmitting the first set of clinical settings to the medical device based on a determination that the medical device does not have the first set of clinical settings. In one embodiment, the method further comprises, subsequent to transmitting the one or more settings to the medical device, receive another request to connect to the server from the medical device, and refraining from transmitting the first set of clinical settings to the medical device based on a determination that the medical device already has the first set of clinical settings. In one embodiment, the one or more settings transmitted to the medical device comprise a Wi-Fi setting usable by the medical device to connect to a Wi-Fi network associated with the remote server.

Other Considerations

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth.

Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a", "an", or "the" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be implemented within a form that does not provide all of the features and benefits set forth herein, as some features can be used or practiced separately from others. All such modifications and variations are intended to be included herein within the scope of this disclosure. Further, additional embodiments created by combining any two or more features or techniques of one or more embodiments described herein are also intended to be included herein within the scope of this disclosure.

What is claimed is:

1. A system configured to update medical device settings, the system comprising:

a location detection system configured to monitor location information associated with a plurality of medical devices and to manage a plurality of geo-fenced areas;

a first server configured to update configuration information stored on one or more medical devices of the plurality of medical devices that are in a first geo-fenced area; and a second server configured to update configuration information stored on one or more medical devices of the plurality of medical devices that are in a second geo-fenced area different from the first geo-fenced area, wherein the location detection system is further configured to:

determine that a first medical device has entered the second geo-fenced area, the first medical device including a first set of network settings usable to communicate with the first server and a first set of clinical settings usable to perform infusion therapies in the first geo-fenced area, wherein the first server is further configured to:

determine that the first medical device has been detected in the second geo-fenced area that is not associated with the first server while still being connected to the first server and in response to the determination that the first medical device has been detected in the second geo-fenced area, transmit, to the first medical device, an instruction to connect to the second server that is associated with the second geo-fenced area, in which the first medical device is detected, along with a second set of network settings usable to disconnect from the first server and to communicate with the second server, and wherein the second server is further configured to:

in response to a connection request from the first medical device, determine that the first set of clinical settings stored on the first medical device need to be updated; and transmit, to the first medical device, a second set of clinical settings usable to perform infusion therapies in the second geo-fenced area that is different from the first set of clinical settings usable to perform infusion therapies in the first geo-fenced area.

2. The system of claim 1, wherein the second server is further configured to transmit an instruction to the first medical device to initiate an infusion therapy to a patient in the second geo-fenced area using the second set of clinical settings.

3. The system of claim 1, wherein the first server is further configured to, in response to a connection request from the first medical device, determine that the second set of clinical settings stored on the first medical device need to be updated, and transmit, to the first medical device, the first set of clinical settings previously stored on the first medical device.

4. The system of claim 1, wherein the first server is further configured to transmit, along with the second set of network settings, a Wi-Fi setting usable by the first medical device to connect to a Wi-Fi network associated with the second server.

5. A server configured to update configuration information stored on one or more medical devices in a first geo-fenced area, the server configured to:

receive a request to connect to the server from a medical device configured to perform clinical operations;

transmit, to the medical device, a first set of clinical settings usable to perform the clinical operations in the first geo-fenced area;

determine that the medical device has performed an infusion therapy in the first geo-fenced area using at least part of the first set of clinical settings transmitted to the medical device;

determine that the medical device has been detected in a second geo-fenced area that is not associated with the server while still being connected to the server; and transmit, to the medical device, an instruction to the medical device to connect to a remote server that is associated with the second geo-fenced area, in which the medical device is detected, along with one or more settings that are usable by the medical device to disconnect from the server and to connect to the remote server.

6. The server of claim 5, wherein the server is further configured to, prior to transmitting the first set of settings to the medical device, determine that the medical device does not have at least some of the first set of settings usable to perform the clinical operations in the first geo-fenced area.

7. The server of claim 5, wherein the server is further configured to transmit an instruction to initiate an infusion in the first geographical area geo-fenced area.

8. The server of claim 5, wherein the server is further configured to, subsequent to transmitting the one or more settings to the medical device, determine that the medical device is no longer connected to the server.

9. The server of claim 5, wherein the server is further configured to determine that the medical device has entered the second geo-fenced area associated with the remote server based on a notification generated by a location detection system configured to detect that the medical device has entered the second-geo-fenced area.

10. The server of claim 5, wherein the server is further configured to, subsequent to transmitting the one or more settings to the medical device, receive another request to connect to the server from the medical device, and transmit the first set of clinical settings to the medical device based on a determination that the medical device does not have the first set of clinical settings.

11. The server of claim 5, wherein the server is further configured to, subsequent to transmitting the one or more settings to the medical device, receive another request to connect to the server from the medical device, and refrain from transmitting the first set of clinical settings to the medical device based on a determination that the medical device already has the first set of clinical settings.

12. The server of claim 5, wherein the one or more settings transmitted to the medical device comprise a Wi-Fi setting usable by the medical device to connect to a Wi-Fi network associated with the remote server.

13. A method of updating configuration information stored on one or more medical devices in a first geo-fenced area, the method comprising:

receiving a request to connect to the server from a medical device configured to perform clinical operations;

transmitting, to the medical device, a first set of clinical settings usable to perform the clinical operations in the first geo-fenced area;

receiving an indication that the medical device has performed an infusion therapy in the first geo-fenced area using at least part of the first set of clinical settings transmitted to the medical device;

receiving an indication that the medical device has been detected in a second geo-fenced area that is not associated with the server while still being connected to the server; and transmitting, to the medical device, an instruction to the medical device to connect to a remote server that is associated with the second geo-fenced area, in which the medical device is detected, along with one or more settings that are usable by the medical device to disconnect from the server and to connect to the remote server.

14. The method of claim 13, further comprising, prior to transmitting the first set of settings to the medical device, determining that the medical device does not have at least some of the first set of settings usable to perform the clinical operations in the first geo-fenced area.

15. The method of claim 13, further comprising transmitting an instruction to initiate an infusion therapy to a patient in the first geo-fenced area.

16. The method of claim 13, further comprising, subsequent to transmitting the one or more settings to the medical device, determining that the medical device is no longer connected to the server.

17. The method of claim 13, further comprising determining that the medical device has entered the second geo-fenced area associated with the remote server based on a notification generated by a location detection system configured to detect that the medical device has entered the second geo-fenced area.

18. The method of claim 13, further comprising, subsequent to transmitting the one or more settings to the medical device, receiving another request to connect to the server from the medical device, and transmitting the first set of clinical settings to the medical device based on a determination that the medical device does not have the first set of clinical settings.

19. The method of claim 13, further comprising, subsequent to transmitting the one or more settings to the medical device, receive another request to connect to the server from the medical device, and refraining from transmitting the first set of clinical settings to the medical device based on a determination that the medical device already has the first set of clinical settings.

20. The method of claim 13, wherein the one or more settings transmitted to the medical device comprise a Wi-Fi setting usable by the medical device to connect to a Wi-Fi network associated with the remote server.

* * * * *